US012159387B2

(12) United States Patent
Matsumoto

(10) Patent No.: US 12,159,387 B2
(45) Date of Patent: Dec. 3, 2024

(54) INSPECTION SUPPORT APPARATUS, INSPECTION SUPPORT METHOD, AND INSPECTION SUPPORT PROGRAM FOR CONCRETE STRUCTURE

(71) Applicant: FUJIFILM Corporation, Tokyo (JP)

(72) Inventor: Kazuma Matsumoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 760 days.

(21) Appl. No.: 17/318,794

(22) Filed: May 12, 2021

(65) Prior Publication Data
US 2021/0272272 A1 Sep. 2, 2021

Related U.S. Application Data

(63) Continuation of application No. PCT/JP2019/042430, filed on Oct. 29, 2019.

(30) Foreign Application Priority Data

Nov. 29, 2018 (JP) ................. 2018-223785

(51) Int. Cl.
G06T 7/00 (2017.01)
E01D 22/00 (2006.01)
(Continued)

(52) U.S. Cl.
CPC .............. G06T 7/0004 (2013.01); G06T 7/40 (2013.01); G06T 7/50 (2017.01); G06T 7/62 (2017.01);
(Continued)

(58) Field of Classification Search
CPC ........... G06T 7/0004; G06T 7/40; G06T 7/50; G06T 7/62; G06T 7/90;
(Continued)

(56) References Cited

U.S. PATENT DOCUMENTS 9,898,676 B2 * 2/2018 Lin ...................... G06V 20/588
9,922,412 B1 * 3/2018 Freeman ................ G06Q 50/16
(Continued)

FOREIGN PATENT DOCUMENTS

CN 108027301 A 5/2018
EP 3 352 129 A1 7/2018
(Continued)

OTHER PUBLICATIONS

An Office Action mailed by China National Intellectual Property Administration on Aug. 9, 2023, which corresponds to Chinese Patent Appliation No. 201980078622.7 and is related to U.S. Appl. No. 17/318,794; with English language translation.
(Continued)

Primary Examiner — Michael S Osinski
(74) Attorney, Agent, or Firm — Studebaker & Brackett PC

(57) ABSTRACT

An inspection support apparatus includes: an image acquisition unit (11) that acquires an image obtained by photographing a concrete structure that is an inspection target; a damage region extraction unit (12) that extracts from the acquired image, a damage region (water leakage, free lime, etc.) appearing on a surface of the concrete structure; a causal part detection unit (17) that detects, in a case where the damage region is extracted, a causal part (a crack, a construction joint, a joint, a peeling part, etc.) causing damage from the image on the basis of a result of extraction of the damage region; and an output unit (19) that outputs the result of extraction of the damage region and a result of detection of the causal part.

17 Claims, 17 Drawing Sheets

(51) Int. Cl.
*G06T 7/40* (2017.01)
*G06T 7/50* (2017.01)
*G06T 7/62* (2017.01)
*G06T 7/90* (2017.01)
*G06V 10/764* (2022.01)
*G06V 10/82* (2022.01)

(52) U.S. Cl.
CPC .............. *G06T 7/90* (2017.01); *G06V 10/764* (2022.01); *G06V 10/82* (2022.01); *E01D 22/00* (2013.01); *G06T 2207/10024* (2013.01); *G06T 2207/30132* (2013.01)

(58) Field of Classification Search
CPC . G06T 2207/10024; G06T 2207/30132; G06T 2207/20081; G06T 7/0008; G06T 2207/30164; G06T 7/0002; G06T 2207/10004; G06T 2207/20076; G06T 2207/20084; G06T 2207/20164; G06T 2207/30108; G06T 2207/30136; G06T 2207/30161; G06T 2207/30252; G06T 7/11; G06V 10/764; G06V 10/82; G06V 10/255; G06V 2201/06; E01D 22/00; C04B 40/0096; G01N 33/383; G01N 2021/8874; G01N 2021/8887; G01N 21/88

See application file for complete search history.

(56) References Cited

U.S. PATENT DOCUMENTS

| | | | | |
|---|---|---|---|---|
| 10,726,558 | B2* | 7/2020 | Ruda | G06T 7/001 |
| 10,937,144 | B2* | 3/2021 | Starr | G06T 7/0004 |
| 11,176,650 | B2* | 11/2021 | Kurita | G06V 30/19173 |
| 11,288,789 | B1* | 3/2022 | Chen | G06T 7/001 |
| 11,317,851 | B2* | 5/2022 | Kikuchi | A61B 5/0077 |
| 11,523,013 | B2* | 12/2022 | Yonaha | G06T 5/50 |
| 11,959,862 | B2* | 4/2024 | Horita | E01D 22/00 |
| 2007/0086651 | A1* | 4/2007 | Stephan | A61B 5/442 382/162 |
| 2015/0086083 | A1* | 3/2015 | Chaudhry | G06T 7/001 382/108 |
| 2017/0017830 | A1* | 1/2017 | Hanai | G06V 20/20 |
| 2017/0200058 | A1* | 7/2017 | Lin | H04N 23/73 |
| 2017/0256051 | A1* | 9/2017 | Dwivedi | G06F 3/00 |
| 2017/0293894 | A1* | 10/2017 | Taliwal | G06V 10/82 |
| 2018/0165541 | A1* | 6/2018 | Amico | G06V 10/141 |
| 2018/0189749 | A1 | 7/2018 | Takamori et al. | |
| 2018/0217024 | A1 | 8/2018 | Takamori et al. | |
| 2018/0247416 | A1* | 8/2018 | Ruda | G06Q 40/08 |
| 2018/0253839 | A1* | 9/2018 | Zur | A61B 1/000094 |
| 2018/0300864 | A1* | 10/2018 | Baba | G06F 18/2451 |
| 2019/0139215 | A1* | 5/2019 | Starr | G06F 18/2148 |
| 2019/0147586 | A1* | 5/2019 | Ikeda | G06T 7/0004 382/157 |
| 2019/0204292 | A1* | 7/2019 | Mimura | G01N 33/483 |
| 2020/0074560 | A1* | 3/2020 | Xu | G06N 3/08 |
| 2020/0265575 | A1* | 8/2020 | Oota | G01N 21/8851 |
| 2021/0270748 | A1* | 9/2021 | Horita | G01N 21/8803 |
| 2022/0148150 | A1* | 5/2022 | Matsumoto | G06T 11/60 |
| 2022/0222855 | A1* | 7/2022 | Valtonen | H04N 23/617 |
| 2022/0301150 | A1* | 9/2022 | Takeuchi | G01N 21/25 |
| 2023/0080178 | A1* | 3/2023 | Hajjar | G06T 7/0004 382/106 |
| 2023/0214558 | A1* | 7/2023 | Ozeki | G06F 30/27 |
| 2023/0342907 | A1* | 10/2023 | Katsuyama | G06T 7/0004 |

FOREIGN PATENT DOCUMENTS

| | | |
|---|---|---|
| JP | 2000-028540 A | 1/2000 |
| JP | 2006-338312 A | 12/2006 |
| JP | 2014-006222 A | 1/2014 |
| JP | 2016-065809 A | 4/2016 |
| JP | 2017-219314 A | 12/2017 |
| JP | 2018-151215 A | 9/2018 |
| KR | 10-1922831 B1 | 11/2018 |

OTHER PUBLICATIONS

International Search Report issued in PCT/JP2019/042430; mailed Jan. 28, 2020.

International Preliminary Report on Patentability and Written Opinion issued in PCT/JP2019/042430; issued May 25, 2021.

An Office Action; "Notice of Reasons for Refusal", mailed by the Japanese Patent Office on May 16, 2022, which corresponds to Japanese Patent Application No. 2020-558206 and is related to U.S. Appl. No. 17/318,794 with English language translation.

The extended European search report issued by the European Patent Office on Jan. 4, 2022, which corresponds to European Patent Application No. 19890234.8-1210 and is related to U.S. Appl. No. 17/318,794.

* cited by examiner

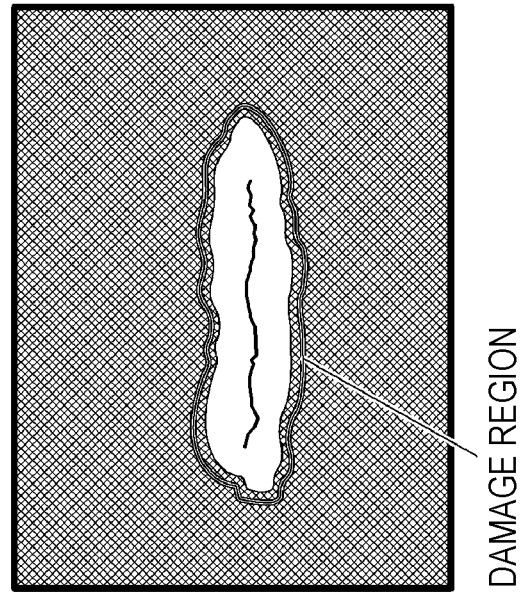
FIG. 2A
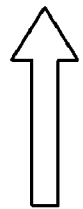
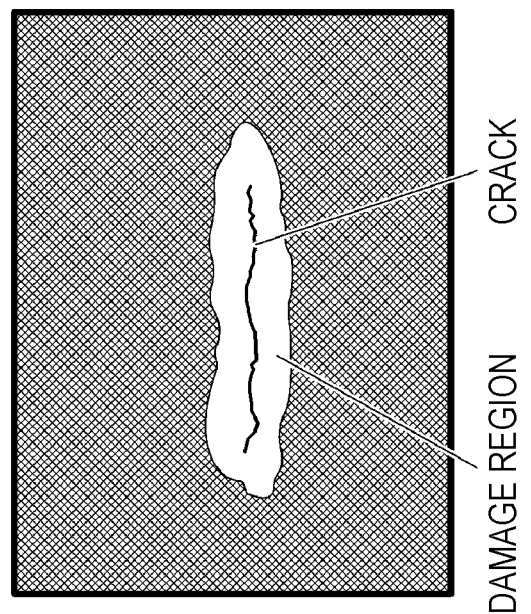
FIG. 2B

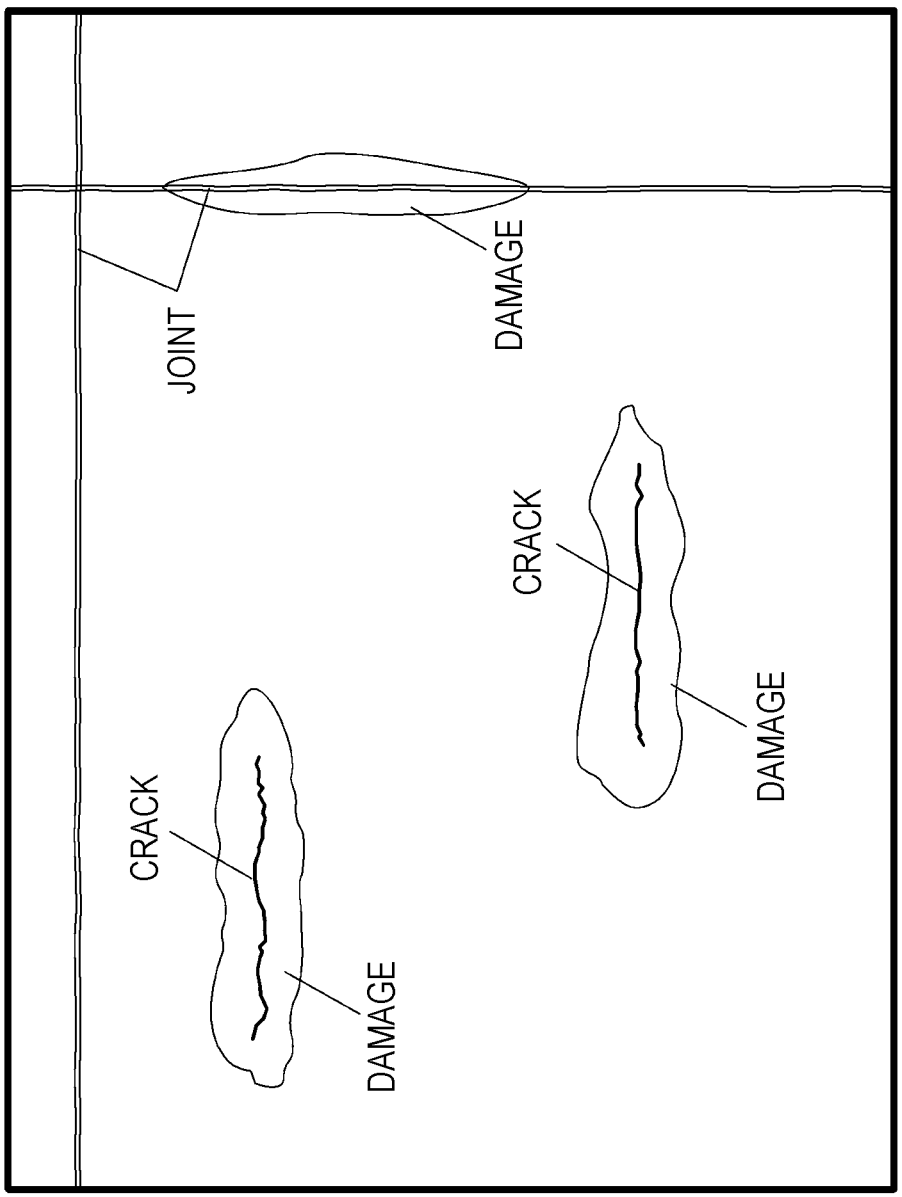

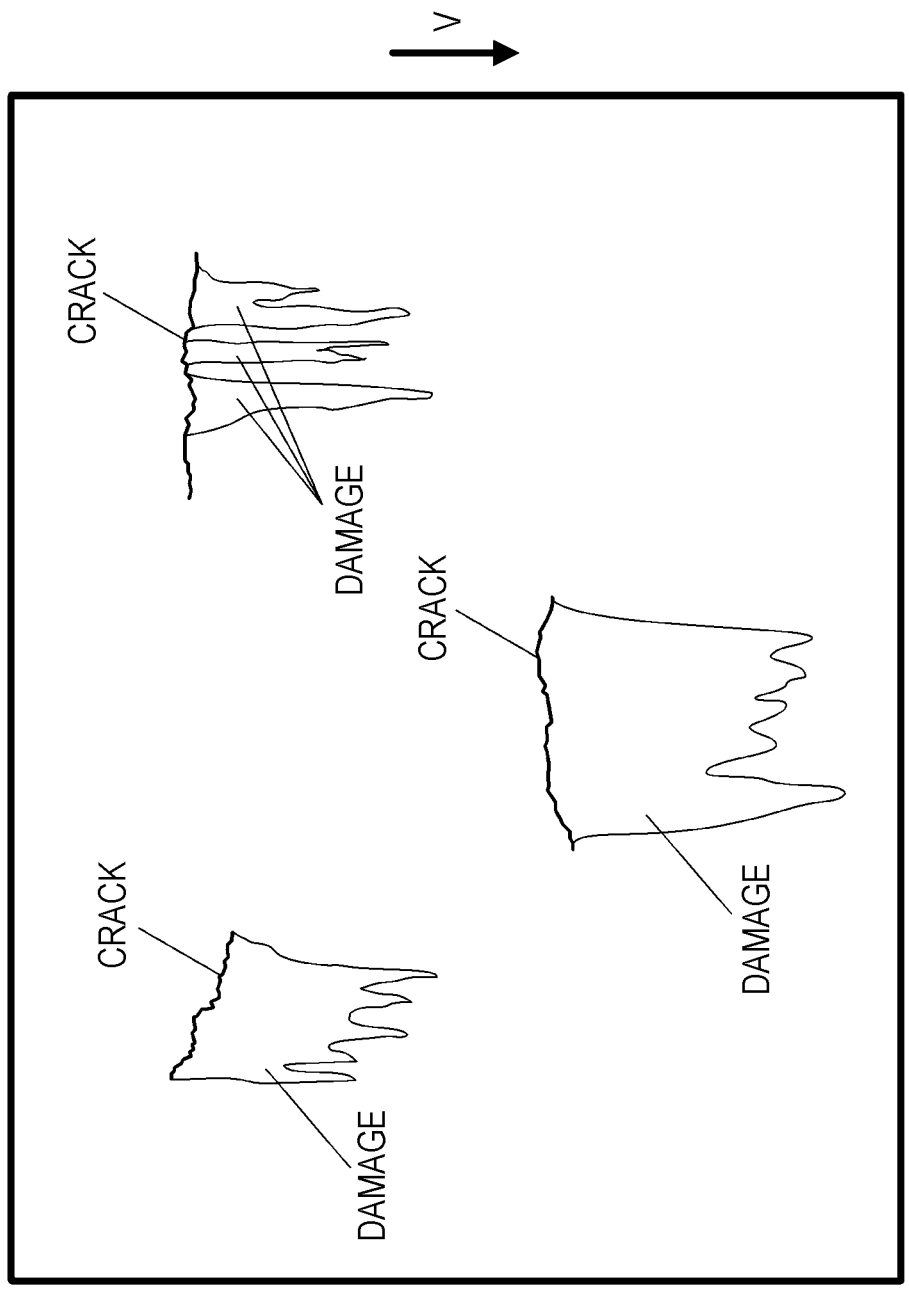

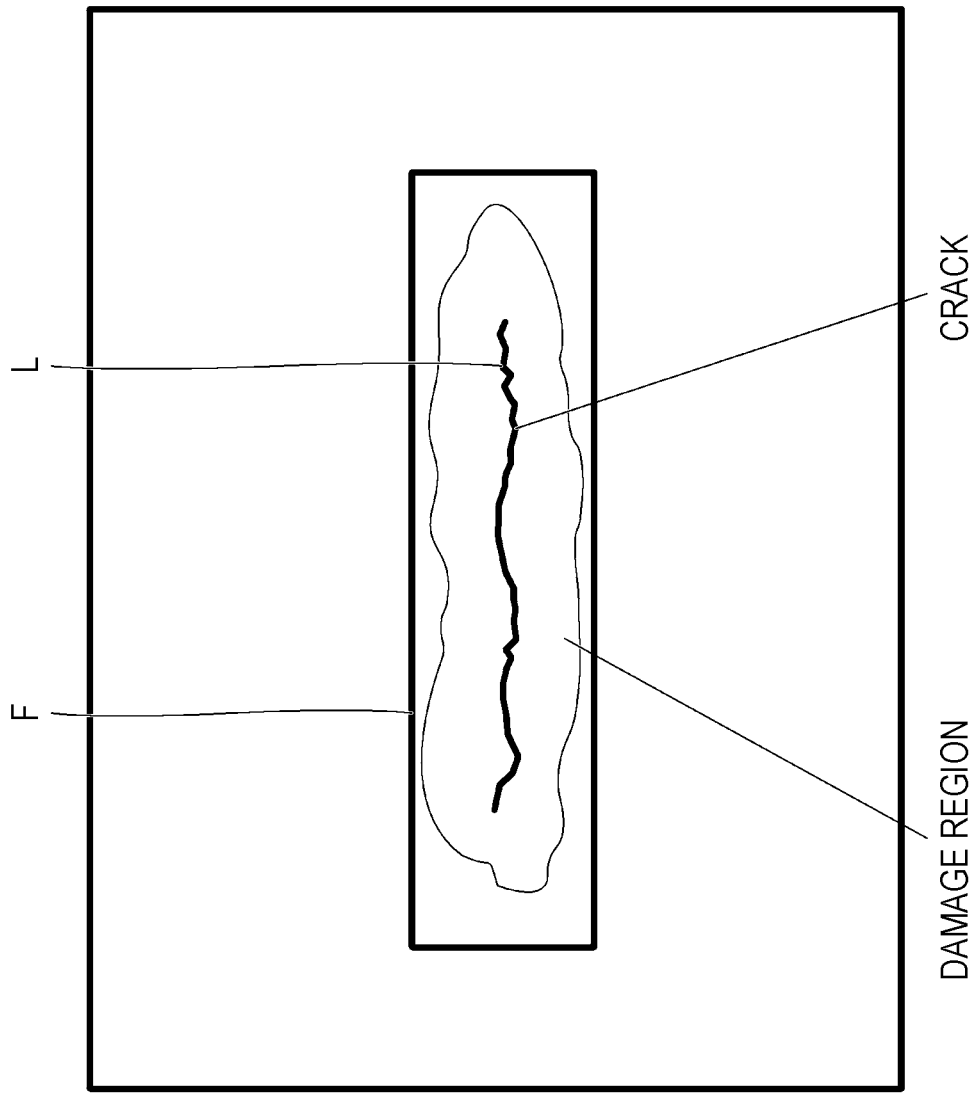

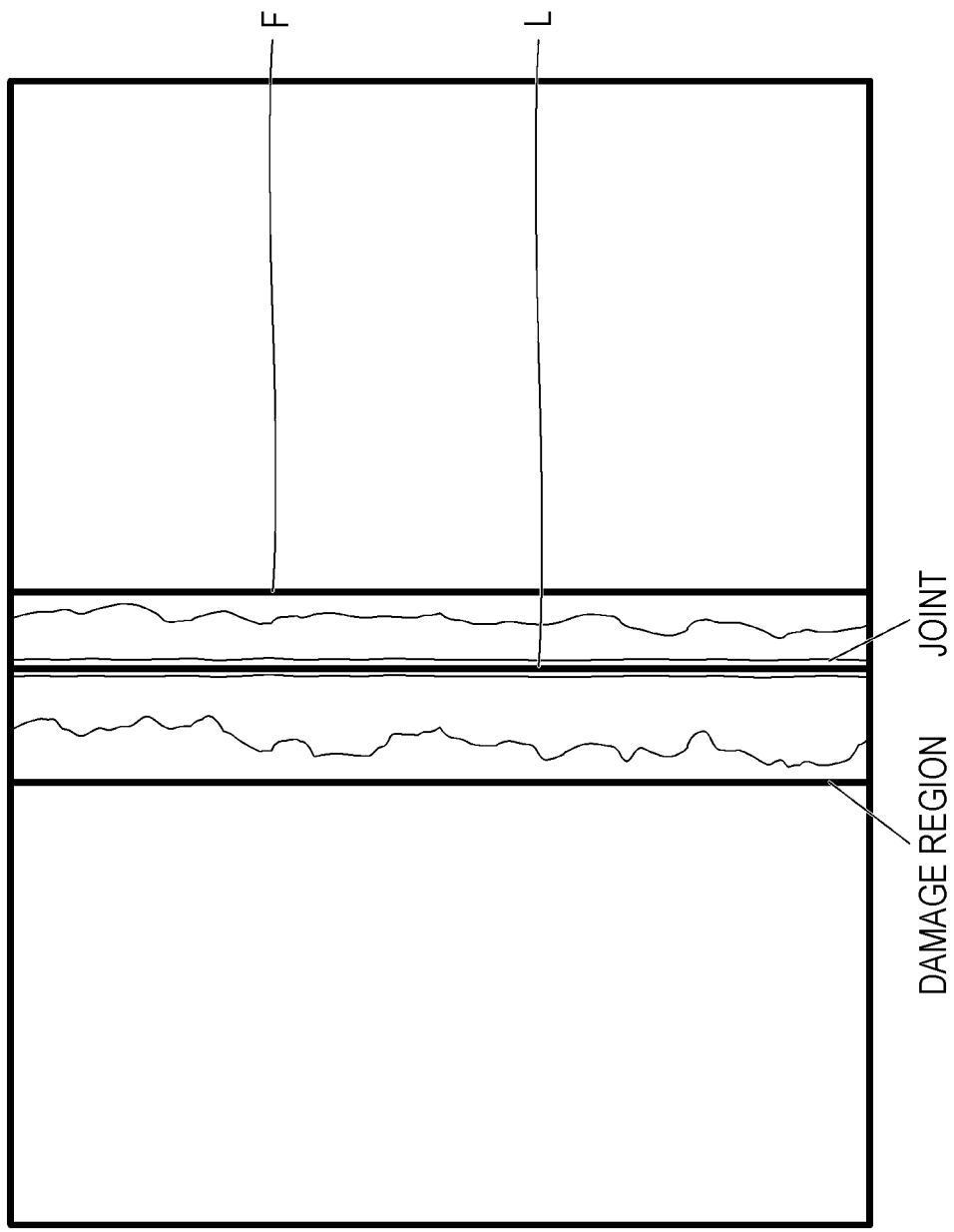

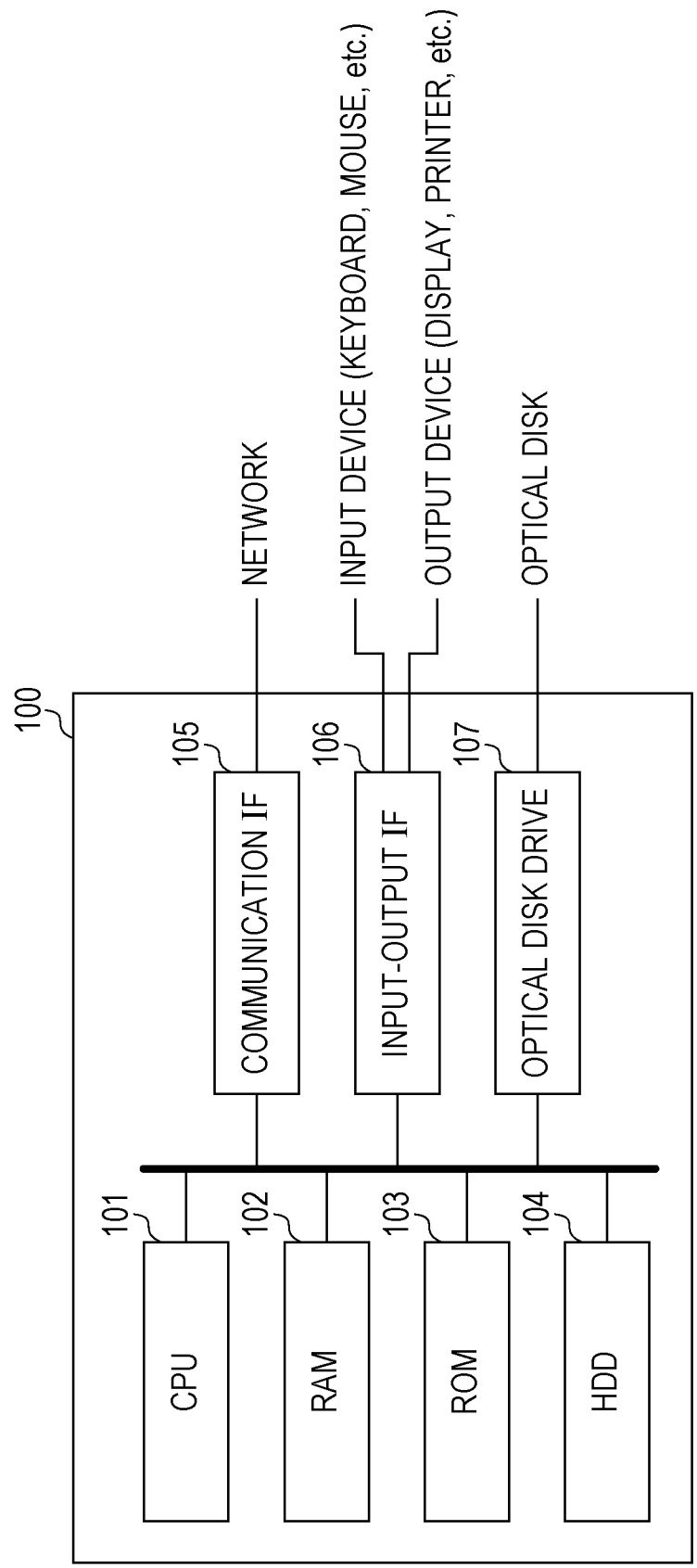

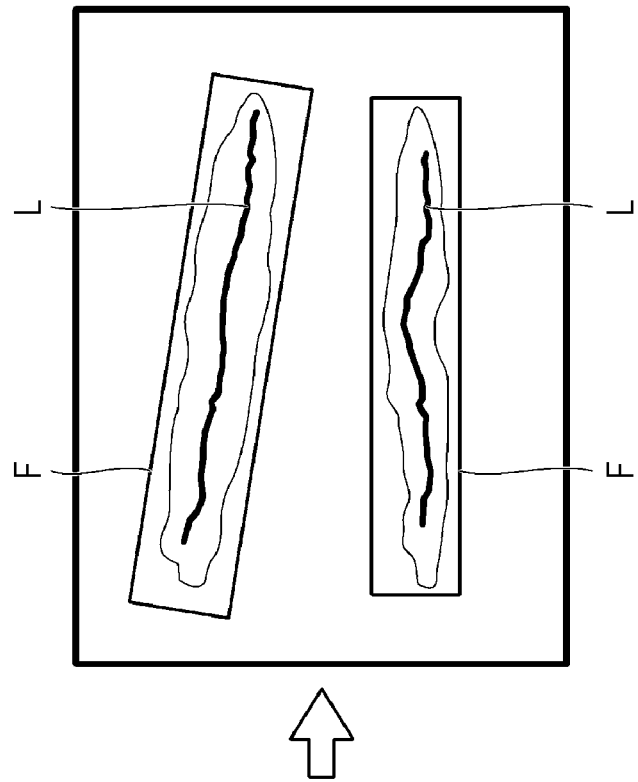
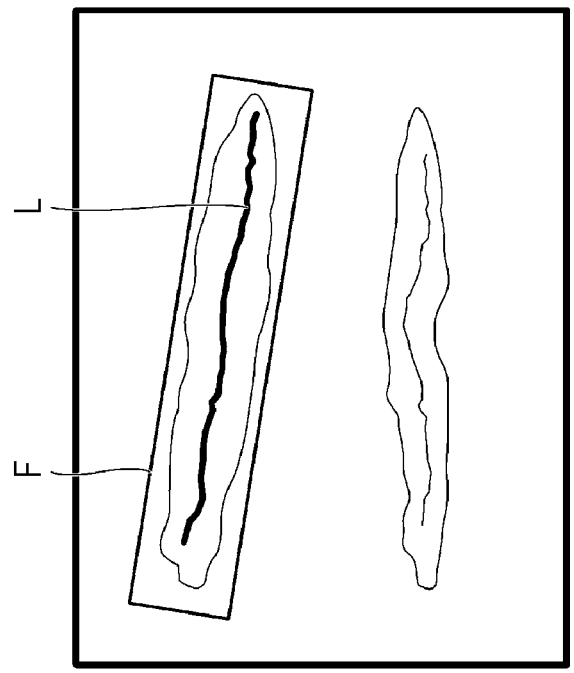

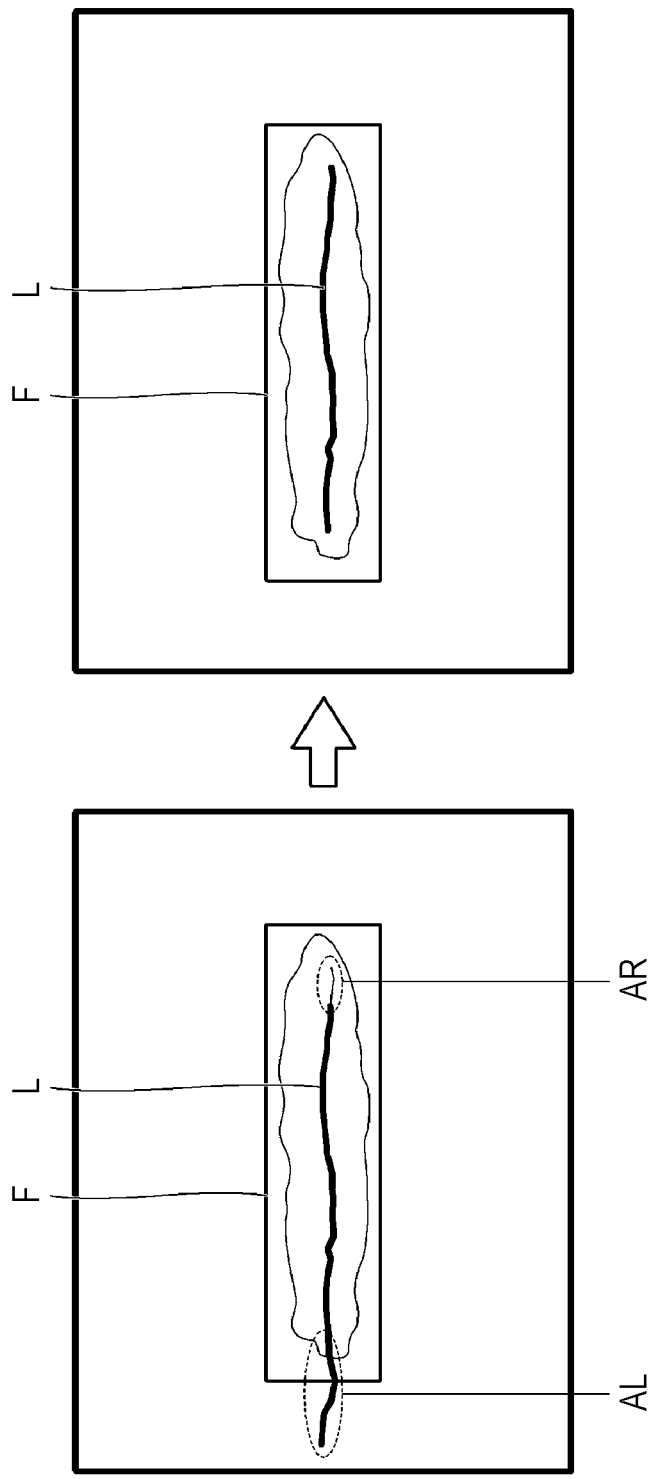

FIG. 13

| DAMAGE REGION ID | TYPE OF DAMAGE | AREA OF DAMAGE REGION (mm$^2$) | CAUSAL PART | WIDTH OF CAUSAL PART (mm) | LENGTH OF CAUSAL PART (mm) | AREA OF CAUSAL PART (mm$^2$) |
|---|---|---|---|---|---|---|
| 1 | WATER LEAKAGE | 19050 | CRACK | 0.2 | 127 | — |
| 2 | WATER LEAKAGE | 113898 | CRACK | 0.2 | 926 | — |
| 3 | FREE LIME | 13050 | CRACK | 0.2 | 90 | — |
| 4 | WATER LEAKAGE | 84736 | JOINT | 0.3 | 331 | — |
| 5 | FREE LIME | 154769 | PEELING | — | — | 84163 |

FIG. 16

| CATEGORY | TYPICAL SITUATION |
|---|---|
| a | NO DAMAGE |
| b | |
| c | WATER LEAKAGE FROM CRACK. ALMOST NO DRIPPING RUST OR FREE LIME OBSERVED. |
| d | FREE LIME FROM CRACK. ALMOST NO DRIPPING RUST OBSERVED. |
| e | CONSIDERABLE WATER LEAKAGE OR FREE LIME (e.g. IN SHAPE OF ICICLES) FROM CRACK, OR CONSIDERABLE MUD OR DRIPPING RUST MIXED INTO WATER LEAKAGE OBSERVED. |

INSPECTION SUPPORT APPARATUS, INSPECTION SUPPORT METHOD, AND INSPECTION SUPPORT PROGRAM FOR CONCRETE STRUCTURE

CROSS-REFERENCE TO RELATED APPLICATIONS

This application is a Continuation of PCT International Application No. PCT/JP2019/042430 filed on Oct. 29, 2019, which claims priority under 35 U.S.C § 119(a) to Japanese Patent Application No. 2018-223785 filed on Nov. 29, 2018. Each of the above application(s) is hereby expressly incorporated by reference, in its entirety, into the present application.

BACKGROUND OF THE INVENTION

1. Field of the Invention

The present invention relates to an inspection support apparatus, an inspection support method, and a non-transitory computer readable recording medium storing an inspection support program for a concrete structure.

2. Description of the Related Art

In an inspection of a concrete structure, such as a bridge, an operation for checking the presence or absence of damage (for example, water leakage, free lime, etc.) is performed. This operation is performed by an inspector approaching and visually inspecting the concrete structure. Such a visual inspection operation involves a large amount of effort.

JP2016-65809A describes a technique in which an inspection support apparatus for a concrete structure acquires an image obtained by photographing a concrete structure that is an inspection target, analyzes the image, and automatically detects damage (the presence or absence of cracks, patterns of cracks, the presence or absence of concrete peeling, the presence or absence of exposure of reinforcing rods, the presence or absence of water leakage, the presence or absence of free lime, the presence or absence of concrete bulging, and the presence or absence of concrete discoloration).

SUMMARY OF THE INVENTION

To make a plan for repairing a concrete structure to which damage has occurred, it is necessary to not only grasp the presence or absence of damage but also identify the cause of the occurring damage (a crack, a construction joint, a joint, peeling, etc.). Accordingly, at the time of inspection, the cause of the occurring damage needs to be investigated.

The present invention has been made in view of the above-described circumstances, and an object thereof is to provide an inspection support apparatus, an inspection support method, and a non-transitory computer readable recording medium storing an inspection support program for a concrete structure, capable of automatically detecting a damage region and a causal part relating to the damage region.

Means for addressing the above-described issue are as follows.

(1) An inspection support apparatus for a concrete structure, the inspection support apparatus including: an image acquisition unit that acquires an image obtained by photographing a concrete structure that is an inspection target; a damage region extraction unit that extracts, from the image, a damage region appearing on a surface of the concrete structure; a causal part detection unit that detects, in a case where the damage region is extracted, a causal part causing damage from the image on the basis of a result of extraction of the damage region; and an output unit that outputs the result of extraction of the damage region and a result of detection of the causal part.

According to this form, the damage region appearing on the surface of the concrete structure is automatically extracted from the image obtained by photographing the concrete structure that is an inspection target. In the case where the damage region is extracted, the causal part causing damage is automatically detected from the image on the basis of the result of extraction of the damage region. Accordingly, the damage region and the causal part relating to the damage region can be automatically detected, and the load of inspection can be reduced.

(2) The inspection support apparatus for a concrete structure according to (1) described above, in which the causal part detection unit detects the causal part from within the damage region.

According to this form, in the case where the damage region is extracted, the causal part is detected from within the damage region.

(3) The inspection support apparatus for a concrete structure according to (1) or (2) described above, further including a photographed-surface-information acquisition unit that acquires information about a photographed surface of the concrete structure, in which the causal part detection unit detects the causal part from the image on the basis of the result of extraction of the damage region and the information about the photographed surface.

According to this form, information about the photographed surface of the concrete structure is acquired, and the information about the photographed surface is used to detect the causal part.

(4) The inspection support apparatus for a concrete structure according to any one of (1) to (3) described above, further including a damaged-surface-information acquisition unit that acquires information about a damaged surface from which the damage region is extracted, in which the causal part detection unit detects the causal part from the image on the basis of the result of extraction of the damage region and the information about the damaged surface.

According to this form, information about the damaged surface from which the damage region is extracted is acquired, and the information about the damaged surface is used to detect the causal part.

(5) The inspection support apparatus for a concrete structure according to (4) described above, in which the damaged-surface-information acquisition unit acquires as the information about the damaged surface, information about a direction of gravity and about an inclination state of the damaged surface relative to the direction of gravity.

According to this form, information about the direction of gravity and about the inclination state of the damaged surface relative to the direction of gravity is acquired as the information about the damaged surface. The damage region is affected by gravity and changes in the way of spreading.

(6) The inspection support apparatus for a concrete structure according to (5) described above, further including a direction-of-gravity determination unit that determines the direction of gravity from the image, in which the damaged-surface-information acquisition unit acquires the information about the direction of gravity from the direction-of-gravity determination unit.

According to this form, the direction of gravity is determined from the acquired image. For example, the direction of gravity is determined by image recognition, etc.

(7) The inspection support apparatus for a concrete structure according to (6) described above, in which the direction-of-gravity determination unit determines the direction of gravity on the basis of a shape of a spread of the damage region and/or a state of damage.

According to this form, the direction of gravity is determined on the basis of the shape of the spread of the damage region and/or the state of damage. The damage region is affected by gravity and changes in the shape of the spread. Therefore, the direction of gravity can be determined from the shape of the spread of the damage region. Further, the state of damage, such as free lime in the shape of icicles, etc., is also affected by gravity. Therefore, the direction of gravity can also be determined from the state of damage.

(8) The inspection support apparatus for a concrete structure according to any one of (5) to (7) described above, further including a damaged-surface inclination state determination unit that determines, from the image, the inclination state of the damaged surface relative to the direction of gravity, in which the damaged-surface-information acquisition unit acquires the information about the inclination state of the damaged surface relative to the direction of gravity from the damaged-surface inclination state determination unit.

According to this form, the inclination state of the damaged surface relative to the direction of gravity is determined from the acquired image. For example, the shape of the spread of the damage region is determined from the image, and the inclination state of the damaged surface is determined from the shape.

(9) The inspection support apparatus for a concrete structure according to any one of (5) to (7) described above, in which the causal part detection unit detects the causal part while a central part of the damage region is weighted in a case where an inclination of the damaged surface is greater than or equal to a threshold value, and detects the causal part while a part on an upper side of the damage region in direction of gravity is weighted in a case where the inclination of the damaged surface is less than the threshold value.

According to this form, in the case where the inclination of the damaged surface is greater than or equal to the threshold value, a central part of the damage region is weighted to detect the causal part. On the other hand, in the case where the inclination of the damaged surface is less than the threshold value, a part on the upper side of the damage region in the direction of gravity is weighted to detect the causal part. That is, in the case where the damaged surface is at a right angle or at close to a right angle to the direction of gravity, a central part of the damage region is weighted to detect the causal part. This is because in such a case, the probability of the causal part being present in a central part of the damage region is high. On the other hand, in the case where the damaged surface is not at a right angle to the direction of gravity (excluding the case where the damaged surface is at close to a right angle to the direction of gravity), a part on the upper side of the damage region in the direction of gravity is weighted to detect the causal part. This is because in such a case, the probability of the causal part being present in a part on the upper side of the damage region in the direction of gravity is high.

(10) The inspection support apparatus for a concrete structure according to any one of (1) to (9) described above, in which the damage region extraction unit extracts the damage region on the basis of a brightness distribution and/or an RGB-value distribution of the image.

According to this form, the damage region is extracted on the basis of the brightness distribution and/or the RGB-value distribution of the image. The damage region has a brightness distribution and an RGB-value distribution different from those of the other region. Therefore, the damage region can be extracted on the basis of the brightness distribution and/or the RGB-value distribution of the image.

(11) The inspection support apparatus for a concrete structure according to any one of (1) to (10) described above, in which the damage region extraction unit extracts as the damage region, a free lime region and/or a water leakage region appearing on the surface of the concrete structure.

According to this form, the free lime region and/or the water leakage region appearing on the surface of the concrete structure can be extracted as the damage region.

(12) The inspection support apparatus for a concrete structure according to any one of (1) to (11) described above, in which the causal part detection unit detects as the causal part, at least one of a crack part, a construction joint part, a joint part, or a peeling part.

According to this form, at least one of a crack part, a construction joint part, a joint part, or a peeling part is detected as the causal part.

(13) The inspection support apparatus for a concrete structure according to any one of (1) to (12) described above, further including a composite image generation unit that generates a composite image obtained by adding a frame that surrounds the damage region and a line that traces the causal part to the image, in which the output unit outputs the composite image to a display device as the result of extraction of the damage region and the result of detection of the causal part.

According to this form, the composite image obtained by adding the frame surrounding the damage region and the line tracing the causal part to the image is generated and output to the display device. Accordingly, the damage region and the causal part can be grasped at a glance.

(14) The inspection support apparatus for a concrete structure according to (13) described above, further including a correction unit that corrects the result of extraction of the damage region and the result of detection of the causal part.

According to this form, the function of correcting the result of extraction of the damage region and the result of detection of the causal part is included. Accordingly, erroneous extraction and erroneous detection can be corrected as appropriate.

(15) The inspection support apparatus for a concrete structure according to any one of (1) to (14) described above, further including a quantification unit that quantifies the damage region and/or the causal part, in which the output unit further outputs information about the quantified damage region and/or the quantified causal part.

According to this form, the damage region and/or the causal part are quantified and output.

(16) The inspection support apparatus for a concrete structure according to (15) described above, in which the quantification unit quantifies the damage region by obtaining an area and/or a color of the damage region, and quantifies the causal part by obtaining at least one of a width, a length, or an area of the causal part.

According to this form, the area and/or the color of the damage region are obtained to quantify the damage region.

Further, at least one of the width, the length, or the area of the causal part is obtained to quantify the causal part.

(17) The inspection support apparatus for a concrete structure according to any one of (1) to (16) described above, further including a degree-of-damage determination unit that determines a degree of damage on the basis of the result of extraction of the damage region and the result of detection of the causal part.

According to this form, the degree of damage is automatically determined on the basis of the result of extraction of the damage region and the result of detection of the causal part.

(18) The inspection support apparatus for a concrete structure according to any one of (1) to (16) described above, further including a damage state determination unit that determines a damage state from the image in a case where the damage region is extracted.

According to this form, in the case where the damage region is extracted, the damage state is determined from the image. For example, for water leakage, the presence or absence of dripping rust, the presence or absence of mixed mud, etc. is determined, and for free lime, the shape of the free lime (the shape of icicles, etc.) is determined.

(19) The inspection support apparatus for a concrete structure according to (18) described above, further including a degree-of-damage determination unit that determines a degree of damage on the basis of the result of extraction of the damage region, the result of detection of the causal part, and a result of determination of the damage state.

According to this form, the degree of damage is determined on the basis of the result of extraction of the damage region, the result of detection of the causal part, and the result of determination of the damage state.

(20) An inspection support method for a concrete structure, the inspection support method including: a step of acquiring an image obtained by photographing a concrete structure that is an inspection target; a step of extracting, from the image, a damage region appearing on a surface of the concrete structure; a step of detecting, in a case where the damage region is extracted, a causal part causing damage from the image on the basis of a result of extraction of the damage region; and a step of outputting the result of extraction of the damage region and a result of detection of the causal part.

According to this form, the damage region appearing on the surface of the concrete structure is extracted from the image obtained by photographing the concrete structure that is an inspection target. In the case where the damage region is extracted, the causal part causing damage is detected from the image on the basis of the result of extraction of the damage region. Accordingly, the damage region and the causal part relating to the damage region can be automatically detected, and the load of inspection can be reduced.

(21) A non-transitory computer readable recording medium storing an inspection support program for a concrete structure, the inspection support program causing a computer to implement: a function of acquiring an image obtained by photographing a concrete structure that is an inspection target; a function of extracting, from the image, a damage region appearing on a surface of the concrete structure; a function of detecting, in a case where the damage region is extracted, a causal part causing damage from the image on the basis of a result of extraction of the damage region; and a function of outputting the result of extraction of the damage region and a result of detection of the causal part.

According to this form, the damage region appearing on the surface of the concrete structure is extracted from the image obtained by photographing the concrete structure that is an inspection target. In the case where the damage region is extracted, the causal part causing damage is detected from the image on the basis of the result of extraction of the damage region. Accordingly, the damage region and the causal part relating to the damage region can be automatically detected, and the load of inspection can be reduced.

According to the present invention, a damage region and a causal part relating to the damage region can be automatically detected.

BRIEF DESCRIPTION OF THE DRAWINGS

FIGS. 2A and 2B are diagrams illustrating example extraction of a damage region;

FIG. 3 is a diagram illustrating an example case of determining the direction of gravity from the shape of damage;

FIG. 4 is a diagram illustrating an example case of determining the direction of gravity from the shape of damage;

FIG. 5 is a diagram illustrating an example composite image;

FIG. 6 is a diagram illustrating an example composite image;

FIG. 7 is a diagram illustrating an example hardware configuration of the inspection support apparatus;

FIGS. 10A and 10B are diagrams illustrating an example correction to a result;

FIGS. 11A and 11B are diagrams illustrating an example correction to a result;

FIG. 13 is a diagram illustrating example quantification;

FIG. 16 is a diagram illustrating example evaluation categories of the degree of damage.

DESCRIPTION OF THE PREFERRED EMBODIMENTS

Hereinafter, preferred embodiments of the present invention will be described in detail with reference to the attached drawings.

First Embodiment

Configuration of Inspection Support Apparatus

An inspection support apparatus 10 of this embodiment is configured as an apparatus that automatically extracts a damage region appearing on a surface of a concrete structure, such as a bridge, from an image, further automatically detects a causal part causing the damage, and outputs the results of extraction and detection.

Figure 1:
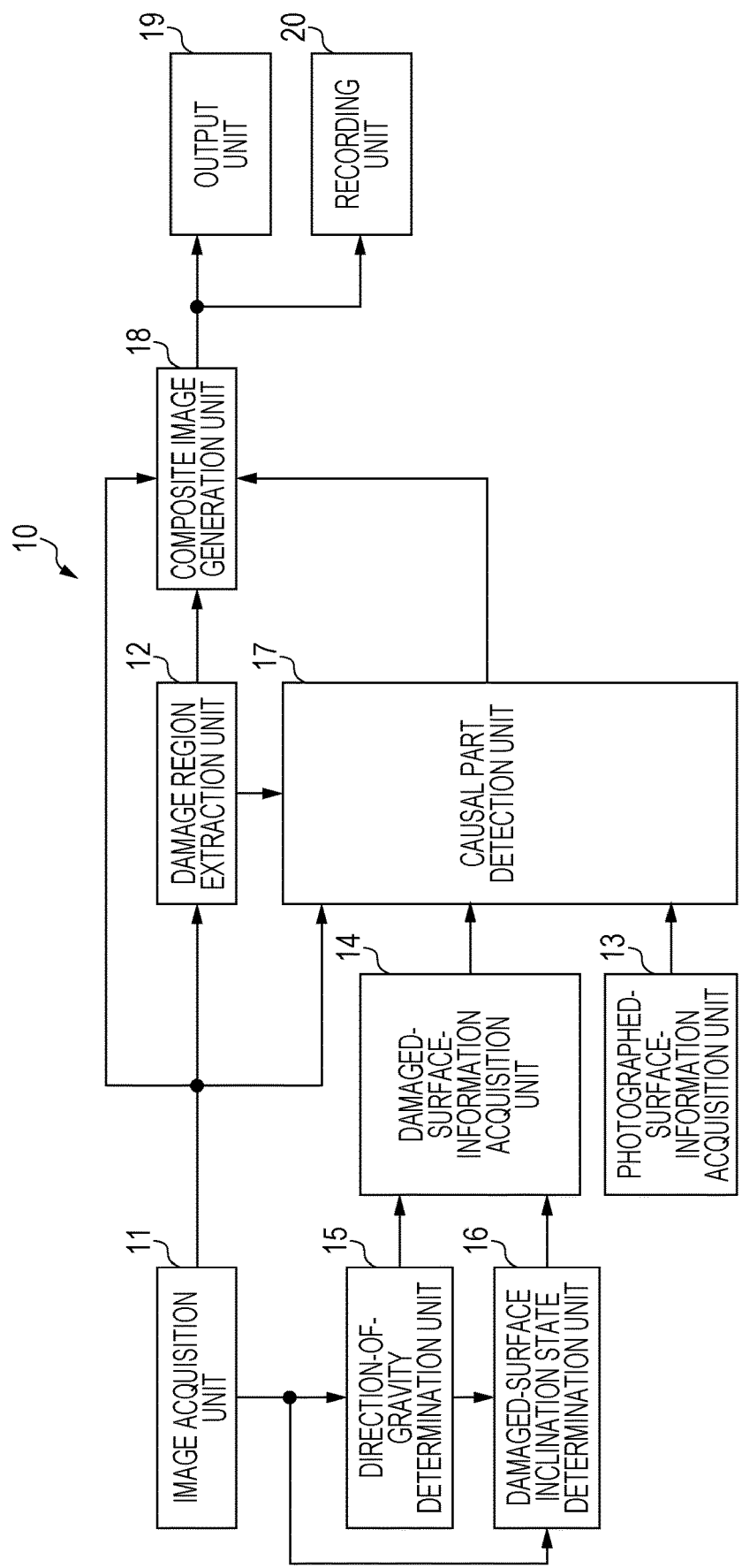
FIG. 1 is a functional block diagram illustrating a first embodiment of an inspection support apparatus.

FIG. 1 is a functional block diagram illustrating a first embodiment of the inspection support apparatus.

As illustrated in FIG. 1, the inspection support apparatus 10 of this embodiment includes an image acquisition unit 11 that acquires an image, a damage region extraction unit 12 that extracts a damage region appearing on a surface of a concrete structure from the acquired image, a photographed-surface-information acquisition unit 13 that acquires information about a photographed surface, a damaged-surface-information acquisition unit 14 that acquires information about a damaged surface, a direction-of-gravity determination unit 15 that determines the direction of gravity (gravity vector) from the acquired image, a damaged-surface inclination state determination unit 16 that determines the inclination state of the damaged surface relative to the direction of gravity from the acquired image, a causal part detection unit 17 that detects a causal part in a case where a damage region is extracted, a composite image generation unit 18 that generates a composite image obtained by combining an image representing the result of extraction of the damage region and the result of detection of the causal part with the acquired image, an output unit 19 that outputs the result of extraction of the damage region and the result of detection of the causal part, and a recording unit 20 that records the result of extraction of the damage region and the result of detection of the causal part in a database.

The image acquisition unit 11 acquires an image obtained by photographing a concrete structure that is an inspection target. The image acquired here is an image (RGB image) in which each pixel has intensity values (brightness values) of R (red), G (green), and B (blue). The image may be an image obtained by photographing the entire surface that is an inspection target or may be an image obtained by photographing only a part of the surface. The image obtained by photographing the entire surface may be an image obtained by dividing the entire surface into a plurality of regions, photographing the regions, and combining the images of the regions into one image (an image obtained by panorama composition).

The damage region extraction unit 12 extracts a damage region appearing on the surface of the concrete structure from the image acquired by the image acquisition unit 11. In the inspection support apparatus 10 of this embodiment, a region in which water leakage (including dripping rust) or free lime is occurring is extracted as a damage region. Here, water leakage is a phenomenon in which water, rainwater, etc. in concrete leaks to the outside through a crack, a construction joint, a joint, a peeling part, etc. Free lime is a phenomenon in which an ingredient of concrete, such as calcium oxide, leaks to the outside together with water, such as rainwater.

The damage region extraction unit 12 extracts a damage region from the image acquired by the image acquisition unit 11 by image recognition. For the image recognition, various methods can be employed.

For example, a method can be employed in which a trained model subjected to machine learning using images that include damage as learning data is used to extract a damage region. The type of machine learning algorithm is not specifically limited and, for example, an algorithm using a neural network, such as an RNN (recurrent neural network), a CNN (convolutional neural network), or an MLP (multilayer perceptron), can be used.

Further, for example, a method in which a damage region is extracted on the basis of the brightness distribution and/or the RGB-value distribution of the image can be employed. A region in which damage is occurring has a brightness distribution and an RGB-value distribution different from those of the other region, and therefore, when changes in the brightness values and/or RGB values are searched for, a damage region can be detected from the image.

FIGS. 2A and 2B are diagrams illustrating example extraction of a damage region. FIG. 2A illustrates an acquired image (an image from which damage is extracted). FIG. 2B is a diagram illustrating example extraction.

As illustrated in FIGS. 2A and 2B, a region in which damage is occurring exhibits features (brightness distribution, RGB-value distribution, etc.) different from those of the other region, and therefore, the damage region can be extracted by image recognition.

In addition to extracting a damage region, the damage region extraction unit 12 determines the type of damage. That is, the damage region extraction unit 12 determines the type of damage, such as water leakage, free lime, etc. This process is performed by using a trained model subjected to machine learning using images that include damage as learning data as in the process for extracting a damage region, or is performed on the basis of, for example, the brightness distribution and/or the RGB-value distribution of the image. Further, other publicly known methods can be employed.

The photographed-surface-information acquisition unit 13 acquires information about a photographed surface of the concrete structure that is an inspection target. The information acquired here includes information with which at least the inclination state of the photographed surface relative to the direction of gravity can be determined. The information with which at least the inclination state of the photographed surface can be determined is information with which it can be determined whether the inclination of the photographed surface relative to the direction of gravity is greater than or equal to a threshold value. This information includes information about the type of photographed surface (for example, ceiling surface, wall surface, etc.) in addition to information indicating whether the inclination of the photographed surface is greater than or equal to the threshold value. Note that the threshold value here is a value for determining whether the inclination of the photographed surface is at a right angle or at close to a right angle to the direction of gravity (in a horizontal state or close to a horizontal state). Therefore, a case where the inclination of the photographed surface is greater than or equal to the threshold value is a case where the photographed surface is at a right angle or at close to a right angle to the direction of gravity.

The information indicating whether the inclination of the photographed surface is greater than or equal to the threshold value is acquired, for example, together with the image of the inspection target. For example, the information is recorded to attached information (attached information conforming to, for example, Exif (Exchangeable image file format) included in the image data, and the information is read from the image and acquired.

The information indicating whether the inclination of the photographed surface is greater than or equal to the threshold value may be recorded after photographing or may be recorded simultaneously with photographing. In a case of recording the information simultaneously with photographing, for example, a photographing device including a function of measuring the inclination of the photographed surface relative to the direction of gravity is used to photograph the inspection target, and the information is recorded together with the image when the captured image is recorded.

The information about the type of photographed surface is, for example, acquired by input from the user. For example, in a case where the inspection target surface is limited to one surface, the type of photographed surface is input, and information about the inclination state of the photographed surface relative to the direction of gravity is acquired. In this case, for example, in a case where the photographed surface is a ceiling, the inclination of the photographed surface relative to the direction of gravity is 90° (at a right angle). In a case where the photographed surface is a wall surface, the inclination of the photographed surface relative to the direction of gravity is 0° (in parallel). Note that a configuration can be employed in which the information about the type of photographed surface is recorded to the attached information for the image and acquired together with the image.

In addition to this, structure information about a concrete structure that is an inspection target can be used to acquire the information about the inclination state of the photographed surface relative to the direction of gravity. The structure information includes information, such as a design drawing, regarding the basic structure of the concrete structure. For example, in a case where the structure information about the inspection target and the photographing position and photographing direction of the image are recorded in association with each other, such information can be used to acquire the information about the inclination state of the photographed surface relative to the direction of gravity.

The damaged-surface-information acquisition unit 14 acquires, in a case where a damage region is extracted, information about a surface (damaged surface) on which damage is appearing. In the inspection support apparatus 10 of this embodiment, as the information about a damaged surface, information about the direction of gravity and about the inclination state of the damaged surface relative to the direction of gravity is acquired. The damaged-surface-information acquisition unit 14 acquires the information about the direction of gravity from the direction-of-gravity determination unit 15 and acquires the information about the inclination state of the damaged surface relative to the direction of gravity from the damaged-surface inclination state determination unit 16.

The direction-of-gravity determination unit 15 determines the direction of gravity (the direction of the gravity vector) from the image acquired by the image acquisition unit 11. To perform the determination, various methods can be employed.

For example, a method can be employed in which a trained model (determiner) subjected to machine learning using a predetermined image group is used to determine the direction of gravity. In this case, for example, a trained model subjected to machine learning using images that include damage as learning data is used to determine the direction of gravity. That is, a determiner is trained and generated so as to determine the direction of gravity from the features of the shape of damage.

Further, for example, a method can be employed in which the direction of gravity is determined on the basis of the shape of the spread of the damage region (the shape of the outline of the damage region) and/or the state of damage. In this case, the shape of the spread of the damage region and/or the state of damage are recognized, and the direction of gravity is determined on the basis of the recognized shape.

FIG. 3 and FIG. 4 are diagrams illustrating example cases of determining the direction of gravity from the shape of the spread of a damage region. FIG. 3 illustrates a damage appearing form in a case where the damaged surface is at a right angle or at close to a right angle to the direction of gravity. FIG. 4 illustrates a damage appearing form in a case where the damaged surface is not at a right angle to the direction of gravity (excluding a case where the damaged surface is at close to a right angle to the direction of gravity).

As illustrated in FIG. 3, in the case where the damaged surface is at a right angle or at close to a right angle to the direction of gravity, the outline of the damage region has a gentle shape or has a shape such that the outline protrudes in a plurality of directions (a shape caused by the fact the direction in which liquids flow is not a certain direction).

On the other hand, as illustrated in FIG. 4, in the case where the damaged surface is not at a right angle to the direction of gravity (the direction of the gravity vector V), the outline of the damage region has a shape such that the outline protrudes in one direction (a shape caused by the fact that liquids flow in the direction of gravity).

Therefore, when a damage region can be recognized from an image, the direction of gravity in the image can be determined from the shape of the outline of the damage region (the shape of the spread of the damage region). The shape of the outline of the damage region is acquired by, for example, approximating the outline of the damage region by a curve. From the acquired curve, the protruding shape is recognized to determine the direction of gravity. That is, in a case where the shape of the outline is a shape such that the outline protrudes in a plurality of directions or the shape of the outline is a gentle shape, it is determined that the direction of gravity is a direction substantially perpendicular to the damaged surface. In a case where the shape of the outline is a shape such that the outline protrudes in one direction, it is determined that the direction of protrusion is the direction of gravity.

The direction of gravity can be determined also from the state of damage. For example, in a case where free lime in the shape of icicles is occurring, the direction of gravity is the direction in which the icicles hang down. Therefore, the direction of gravity can be determined by recognizing the damage state from the image.

The damaged-surface inclination state determination unit 16 determines the inclination state of the damaged surface relative to the direction of gravity from the image acquired by the image acquisition unit 11. Specifically, the damaged-surface inclination state determination unit 16 determines whether the inclination of the damaged surface relative to the direction of gravity is greater than or equal to a threshold value. To perform the determination, various methods can be employed.

For example, as in determination of the direction of gravity, a method can be employed in which a trained model (determiner) subjected to machine learning using a predetermined image group is used to determine whether the inclination of the damaged surface is greater than or equal to the threshold value. In this case, for example, a trained model subjected to machine learning using images that include damage as learning data is used to determine whether the inclination of the damaged surface is greater than or equal to the threshold value. That is, a determiner is trained and generated so as to determine the inclination state of the damaged surface from the features of the shape of damage.

Further, for example, a method can be employed in which the inclination state of the damaged surface is determined from the shape of the spread of the damage region (the shape of the outline of the damage region) and/or the state of damage. In this case, the shape of the spread of the damage region is recognized, and the inclination state of the damaged surface is determined on the basis of the recognized shape. As described above, in the case where the damaged surface is at a right angle or at close to a right angle to the direction of gravity, the outline of the damage region has a gentle shape or has a shape such that the outline protrudes in a plurality of directions (see FIG. 3). On the other hand, in the case where the damaged surface is not at a right angle to the direction of gravity, the outline of the damage region has a shape such that the outline protrudes in one direction (see FIG. 4). Therefore, when a damage region can be recognized from an image, the inclination state of the damaged surface can be determined from the shape of the outline of the damage region. The shape of the outline of the damage region is acquired by, for example, approximating the outline of the damage region by a curve as described above. From the acquired curve, the protruding shape is recognized to determine the inclination state of the damaged surface. That is, in the case where the shape of the outline is a shape such that the outline protrudes in a plurality of directions or the shape of the outline is a gentle shape, it is determined that the inclination of the damaged surface is greater than or equal to the threshold value. In the case where the shape of the outline is a shape such that the outline protrudes in one direction, it is determined that the inclination of the damaged surface is less than the threshold value.

The direction of gravity can be determined also from the state of damage. For example, in the case where free lime in the shape of icicles is occurring as described above, the direction of gravity is the direction in which the icicles hang down. Therefore, the inclination state of the damaged surface can be determined by recognizing the direction in which the icicles hang down.

The causal part detection unit 17 detects, in a case where a damage region is extracted, a part (causal part) that causes the damage from the image on the basis of the result of extraction of the damage region by the damage region extraction unit 12. Water leakage (including dripping rust) and free lime, which are examples of damage, are caused mainly by a crack, a construction joint, a joint, peeling, etc. Therefore, the causal part detection unit 17 detects a part of a crack, a construction joint, a joint, peeling, etc. as a causal part. The causal part detection unit 17 detects a part of a crack, a construction joint, a joint, peeling, etc. by image recognition to thereby detect a causal part.

To detect a causal part, the causal part detection unit 17 uses the information about the photographed surface acquired by the photographed-surface-information acquisition unit 13 and the information about the damaged surface acquired by the damaged-surface-information acquisition unit 14 to detect a causal part. That is, the causal part detection unit 17 uses the information about the direction of gravity in the image and the inclination state of the damaged surface (photographed surface) relative to the direction of gravity to detect a causal part. For example, in a case where the damaged surface (photographed surface) is at a right angle or at close to a right angle to the direction of gravity (in a case where the inclination of the damaged surface is greater than or equal to the threshold value), it is often the case that the causal part is present within the damage region (specifically, in a central part) as illustrated in FIG. 3. Therefore, in this case, the damage region is searched to detect a causal part. In a case where the damaged surface (photographed surface) is not at a right angle to the direction of gravity (in a case where the inclination of the damaged surface is less than the threshold value), it is often the case that the causal part is present on the upper side of the damage region in the direction of gravity (on the start point side of the gravity vector V) as illustrated in FIG. 4. Therefore, in this case, the upper side of the damage region in the direction of gravity is searched to detect a causal part.

Specifically, each region in the image is weighted on the basis of the inclination state of the damaged surface (photographed surface) to detect a crack, a construction joint, a joint, peeling, etc. that may be a causal part. For example, in the case where the damaged surface (photographed surface) is at a right angle or at close to a right angle to the direction of gravity (in the case where the inclination of the damaged surface is greater than or equal to the threshold value), a region inside the damage region is heavily weighted to detect a causal part. Specifically, a central part of the damage region is heavily weighted to detect a causal part. In the case where the damaged surface (photographed surface) is not at a right angle to the direction of gravity (in the case where the inclination of the damaged surface is less than the threshold value), a region on the upper side of the damage region in the direction of gravity (on the start point side of the gravity vector V) is heavily weighted to detect a causal part. As the method for detecting a crack, a construction joint, a joint, peeling, etc. by image recognition, publicly known methods including a method of using a trained model can be employed.

As described above, when a causal part is detected by using information about the direction of gravity in the image and the inclination state of the damaged surface (photographed surface) relative to the direction of gravity, the causal part can be detected efficiently.

In addition to detecting a causal part, the causal part detection unit 17 determines the type of the detected causal part. That is, the causal part detection unit 17 determines the type of cause (crack, construction joint, joint, peeling, etc.) This process is performed by using a trained model subjected to machine learning using images that include damage as learning data or is performed on the basis of, for example, the brightness distribution and/or the RGB-value distribution of the image. Further, other publicly known methods can be employed.

The composite image generation unit 18 generates a composite image obtained by combining an image representing the result of extraction of the damage region and the result of detection of the causal part with the image acquired by the image acquisition unit 11. Specifically, the composite image generation unit 18 generates a composite image obtained by adding a frame that surrounds the damage region and a line that traces the causal part.

FIG. 5 and FIG. 6 are diagrams illustrating example composite images.

FIG. 5 illustrates an example composite image in a case where free lime is caused by a crack. In this case, the region of the free lime is extracted by the damage region extraction unit 12 as a damage region. The part of the crack is detected by the causal part detection unit 17 as a causal part. The composite image generation unit 18 adds a rectangular frame F so as to surround the region in which the free lime occurs, which is the damage region, on the basis of the result of extraction by the damage region extraction unit 12. The composite image generation unit 18 adds a line L that traces the part of the crack, which is the causal part, on the basis of the result of detection by the causal part detection unit 17.

FIG. 6 illustrates example generation of a composite image in a case where free lime is caused by a joint. In this case, the region of the free lime is extracted by the damage region extraction unit 12 as a damage region. The part of the joint is detected by the causal part detection unit 17 as a causal part. The composite image generation unit 18 generates a composite image to which the rectangular frame F is added so as to surround the region in which the free lime occurs, which is the damage region, on the basis of the result of extraction by the damage region extraction unit 12. The composite image generation unit 18 generates a composite image to which the line L that traces the part of the joint, which is the causal part, is added on the basis of the result of detection by the causal part detection unit 17.

In the examples illustrated in FIG. 5 and FIG. 6, a configuration in which the damage region is surrounded by the rectangular frame F is employed; however, the shape of the frame F that surrounds the damage region is not specifically limited. Alternatively, a configuration in which the damage region is surrounded by a circle (including an ellipse) may be employed.

In a case where the type of damage is determined, the color of the frame F may be changed in accordance with the type of damage. For example, a free lime region may be surrounded by the frame F in pink, and a water leakage region may be surrounded by the frame F in blue. Accordingly, the type of damage can be identified with the color of the frame F. Similarly, in a case where the type of causal part is determined, the color of the line L may be changed in accordance with the type of causal part. For example, a crack may be traced by the line L in red, and a joint may be traced by the line L in blue. Accordingly, the type of cause can be identified with the color of the line L.

The output unit 19 outputs the result of extraction of the damage region by the damage region extraction unit 12 and the result of detection, by the causal part detection unit 17, of the causal part causing the damage. In the inspection support apparatus 10 of this embodiment, the composite image generated by the composite image generation unit 18 is output to an external display device as the result of extraction of the damage region and the result of detection of the causal part. Note that the output here may be output via a network.

The recording unit 20 records the result of extraction of the damage region and the result of detection of the causal part to a database. In the inspection support apparatus 10 of this embodiment, the composite image generated by the composite image generation unit 18 is recorded to a database as the result of extraction of the damage region and the result of detection of the causal part. Alternatively, together with image data of the acquired image, data of the result of extraction of the damage region extracted from the image and data of the result of detection of the causal part may be recorded to a database. The data is recorded to, for example, a hard disk drive (HDD).

Hardware Configuration of Inspection Support Apparatus

FIG. 7 is a diagram illustrating an example hardware configuration of the inspection support apparatus.

The inspection support apparatus 10 is implemented by installing an inspection support program in a computer 100. The computer 100 is formed of, for example, a personal computer or a general-purpose computer. The inspection support program is recorded to a recording medium, such as a DVD (digital versatile disc) or a CD-ROM (compact disk read-only memory), and distributed, and is installed in the computer 100 from the recording medium. Alternatively, the inspection support program is downloaded via a network and installed in the computer 100.

The computer 100 includes a CPU (central processing unit) 101, a RAM (random access memory) 102, a ROM (read-only memory) 103, an HDD 104, a communication IF (interface) 105, an input-output IF (interface) 106, and an optical disk drive 107. The computer 100 functions as the inspection support apparatus 10 by the CPU 101 executing the inspection support program.

To the HDD 104, various programs including the inspection support program and various types of data are recorded.

The communication IF 105 transmits and receives data to and from other computers. The communication IF 105 is formed of, for example, a wired or wireless network card.

The input-output IF 106 is connected to an input device and an output device, accepts input by the user, and outputs information for the user. The input device is formed of, for example, a keyboard, a mouse, a touch panel, etc., and the output unit is formed of, for example, a display (display device), a printer, etc.

The optical disk drive 107 reads data recorded to an optical disk, such as a DVD, a CD-ROM, etc., and writes data to the optical disk.

An image obtained by photographing an inspection target is imported into the computer 100, which serves as the inspection support apparatus 10, from an external device (for example, a photographing device, such as a digital camera, a personal computer, etc.) via the communication IF 105. Alternatively, the image is read from the optical disk via the optical disk drive 107 and imported. The image imported into the computer 100 is stored in the HDD 104. Then, the image is read form the HDD 104 and subjected to an inspection support process.

Inspection Support Process

Figure 8:
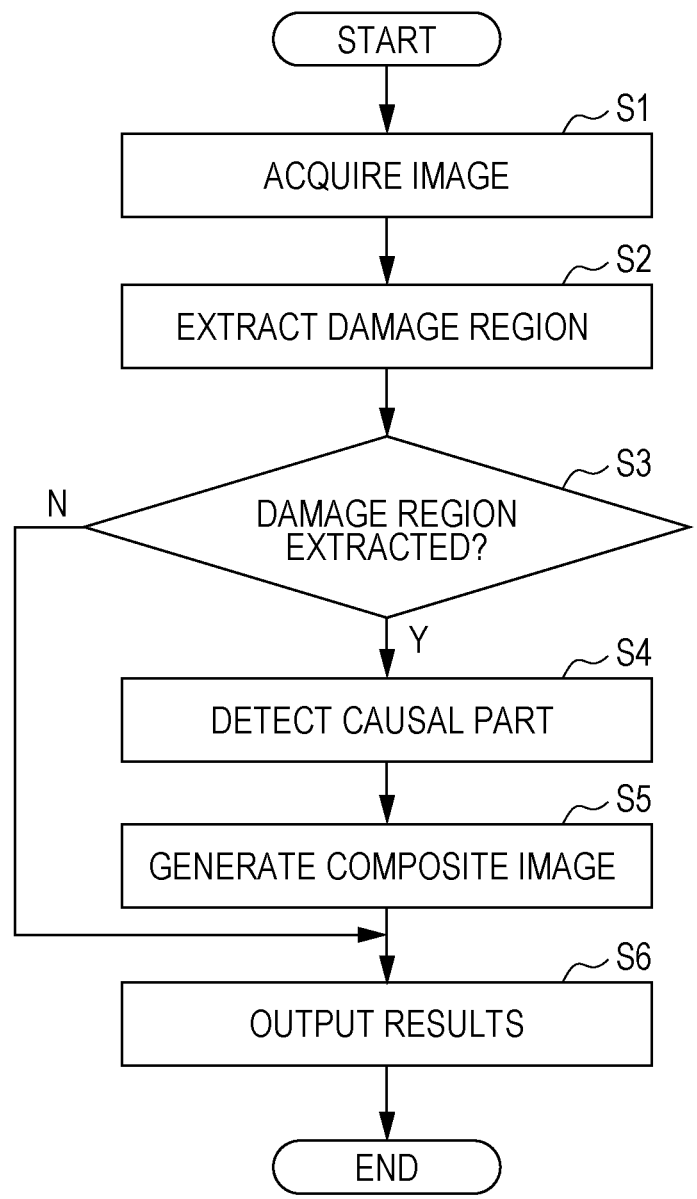
FIG. 8 is a flowchart illustrating a procedure of an inspection support process.

FIG. 8 is a flowchart illustrating a procedure of an inspection support process (inspection support method).

First, an image obtained by photographing a concrete structure that is an inspection target is acquired (step S1). As described above, this image is imported into the inspection support apparatus 10 (computer 100) via a network. Alternatively, the image is imported into the inspection support apparatus 10 via the optical disk drive 107. The imported image is stored in the HDD 104, is read from the HDD 104, and is subjected to processing.

Next, a damage region that appears on a surface of the concrete structure is extracted from the acquired image (step S2). With this process, a damage region of water leakage, free lime, etc. is extracted from the image.

Next, on the basis of the result of the process for extracting a damage region, it is determined whether a damage region is extracted (step S3).

In a case where a damage region is extracted (in a case of "Y" in step S3), subsequently, a causal part is detected the acquired image (step S4). At this time, a causal part is detected on the basis of the result of extraction of the damage region. Further, a causal part is detected by using information about the direction of gravity in the image and the inclination state of the damaged surface (photographed surface). Specifically, in the case where the damaged surface (photographed surface) is at a right angle or at close to a right angle to the direction of gravity (in the case where the inclination of the damaged surface is greater than or equal to the threshold value), a region inside the damage region is heavily weighted to detect a causal part. On the other hand, in the case where the damaged surface (photographed surface) is not at a right angle to the direction of gravity (in the case where the inclination of the damaged surface is less than the threshold value), a region on the upper side of the damage region in the direction of gravity is heavily weighted to detect a causal part.

Next, on the basis of the result of extraction of the damage region and the result of detection of the causal part, a composite image is generated (step S5). Specifically, a composite image obtained by adding the frame F that surrounds the damage region and the line L that traces the causal part to the acquired image is generated (see FIG. 5 and FIG. 6).

Next, the generated composite image is output to a display (display device) as the result of extraction of the damage region and the result of detection of the causal part (step S6). The user can check this display on the display to thereby grasp damage (water leakage, free lime, etc.) occurring on the surface of the concrete structure that is an inspection target and the cause of the damage (a crack, a construction joint, a joint, a peeling part, etc.).

In a case where a damage region is not extracted (in a case of "N" in step S3), a result indicating "no damage" is output.

The result of extraction of the damage region and the result of detection of the causal part are recorded to the HDD 104 in a database. At this time, together with image data of the acquired image, data of the result of extraction of the damage region extracted from the image data and data of the result of detection of the causal part are recorded.

As described above, with the inspection support apparatus 10 of this embodiment, a damage region can be automatically extracted from an image. In a case where a damage region is extracted, a causal part can be automatically detected. Accordingly, the load of inspection can be significantly reduced.

Second Embodiment

Figure 9:
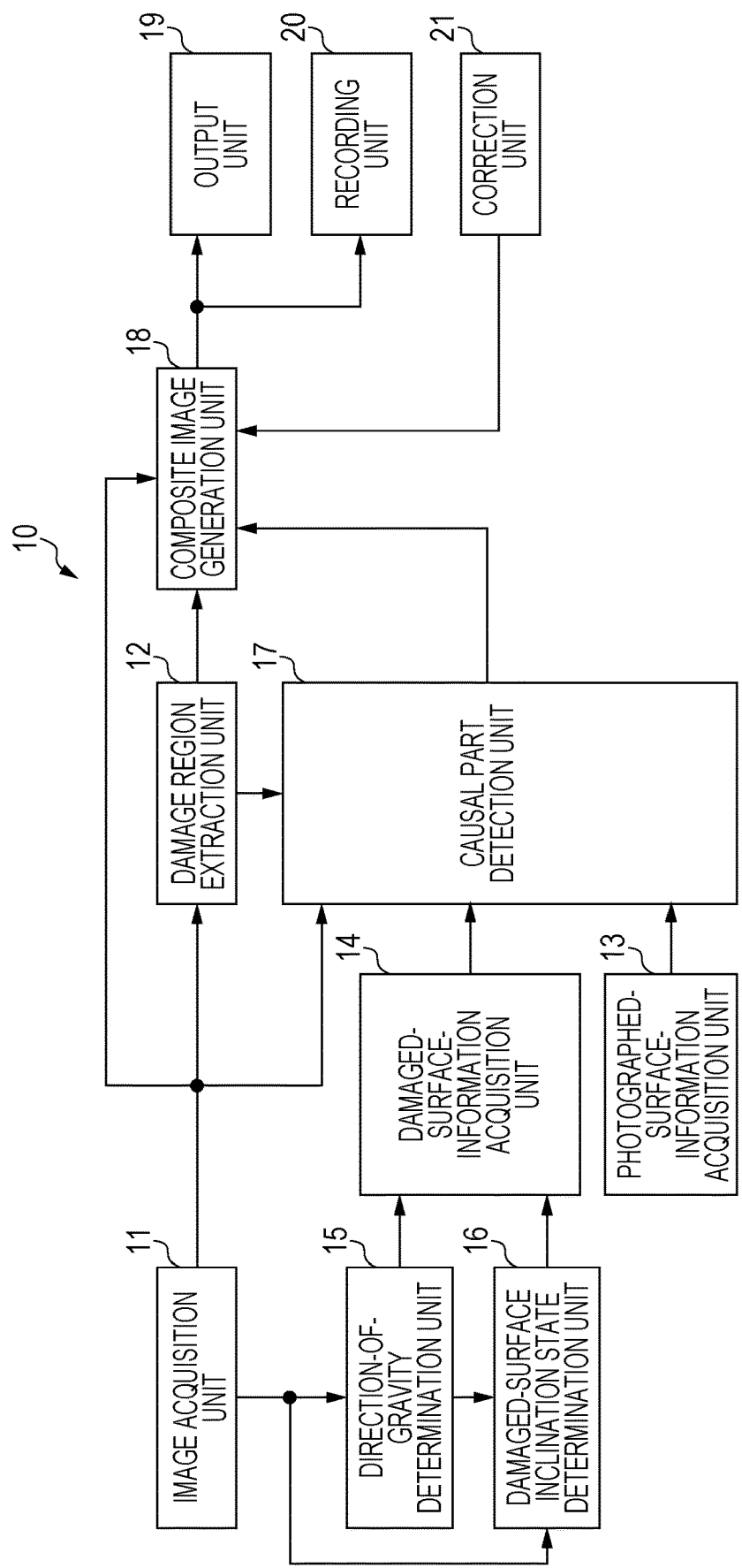
FIG. 9 is a functional block diagram illustrating a second embodiment of the inspection support apparatus.

FIG. 9 is a functional block diagram illustrating a second embodiment of the inspection support apparatus.

The inspection support apparatus 10 of this embodiment is different from the inspection support apparatus 10 of the first embodiment described above in that the inspection support apparatus 10 of this embodiment further includes a correction unit 21 that corrects the result of extraction of a damage region and the result of detection of a causal part. Only the part different from the inspection support apparatus 10 of the above-described first embodiment is described below.

Erroneous detection may occur in extraction of a damage region and detection of a causal part. The inspection support apparatus 10 of this embodiment includes a function of correcting a result in a case where erroneous detection occurs.

The correction unit 21 accepts a correction to the result of extraction of a damage region and the result of detection of a causal part via an input device (a keyboard, a mouse, a touch panel, etc.) and corrects the result of extraction of a damage region and the result of detection of a causal part. For example, the frame F that surrounds a damage region is added, deleted, or resized on the screen of a display on which the composite image is displayed to correct the result of extraction of the damage region. Further, the line L that traces a causal part is added, deleted, or adjusted in fine increments to correct the result of detection of the causal part.

FIGS. 10A and 10B and FIGS. 11A and 11B are diagrams illustrating example corrections to results.

FIGS. 10A and 10B illustrate an example correction to the result of extraction of a damage region. FIG. 10A illustrates a composite image before correction, and FIG. 10B illustrates the composite image after correction.

As illustrated in FIG. 10A, in this example, a damage region that is to be extracted is not extracted. That is, in the image, damage regions are present in two locations, namely, on the upper side and the lower side; however, only the damage region on the upper side is extracted and the damage region on the lower side is not extracted. In such a case where an error occurs in extraction of a damage region, the user, for example, manually adds the frame F as illustrated in FIG. 10B to correct the result of extraction of the damage region. In addition, the user also corrects the result of detection of a causal part. That is, to the newly extracted damage region, the user manually adds the line L that traces the causal part. The user adds the frame F by, for example, specifying and inputting two points on a diagonal line on the screen. Further, the user, for example, enlarges, reduces, moves, or rotates the frame F as necessary to correct the position, size, range, etc. of the frame F.

FIGS. 11A and 11B illustrate an example correction to the result of detection of a causal part. FIG. 11A illustrates a composite image before correction, and FIG. 11B illustrates the composite image after correction.

As illustrated in FIG. 11A, in this example, a causal part is erroneously detected. That is, a causal part that is to be detected is partially omitted (in the circular shape AR represented by a dashed line on the right side of FIG. 11A), and a part that is not to be detected as a causal part is detected as a causal part (in the circular shape AL represented by a dashed line on the left side of FIG. 11A). In such a case where an error occurs in detection of a causal part, the user manually corrects the line L as illustrated in FIG. 11B to correct the result of detection of the causal part. That is, the user deletes an unwanted line segment, adds an omitted line segment, or changes the position of a line segment to thereby correct the result of detection of the causal part.

In a case of recording the result of extraction of the damage region and the result of detection of the causal part, the results obtained after the corrections are recorded.

As described above, with the inspection support apparatus 10 of this embodiment, even in a case where, for example, erroneous detection is occurring, a correction can be easily made. Depending on the type of damage, the causal part may be covered by the damage, and it might not be possible to correctly detect the causal part. In such a case, the inspection support apparatus 10 of this embodiment effectively functions. For example, in a case of free lime caused by a crack, the crack may be covered by the free lime and might not be correctly detected. In such a specific case, the inspection support apparatus 10 of this embodiment effectively functions.

Third Embodiment

Figure 12:
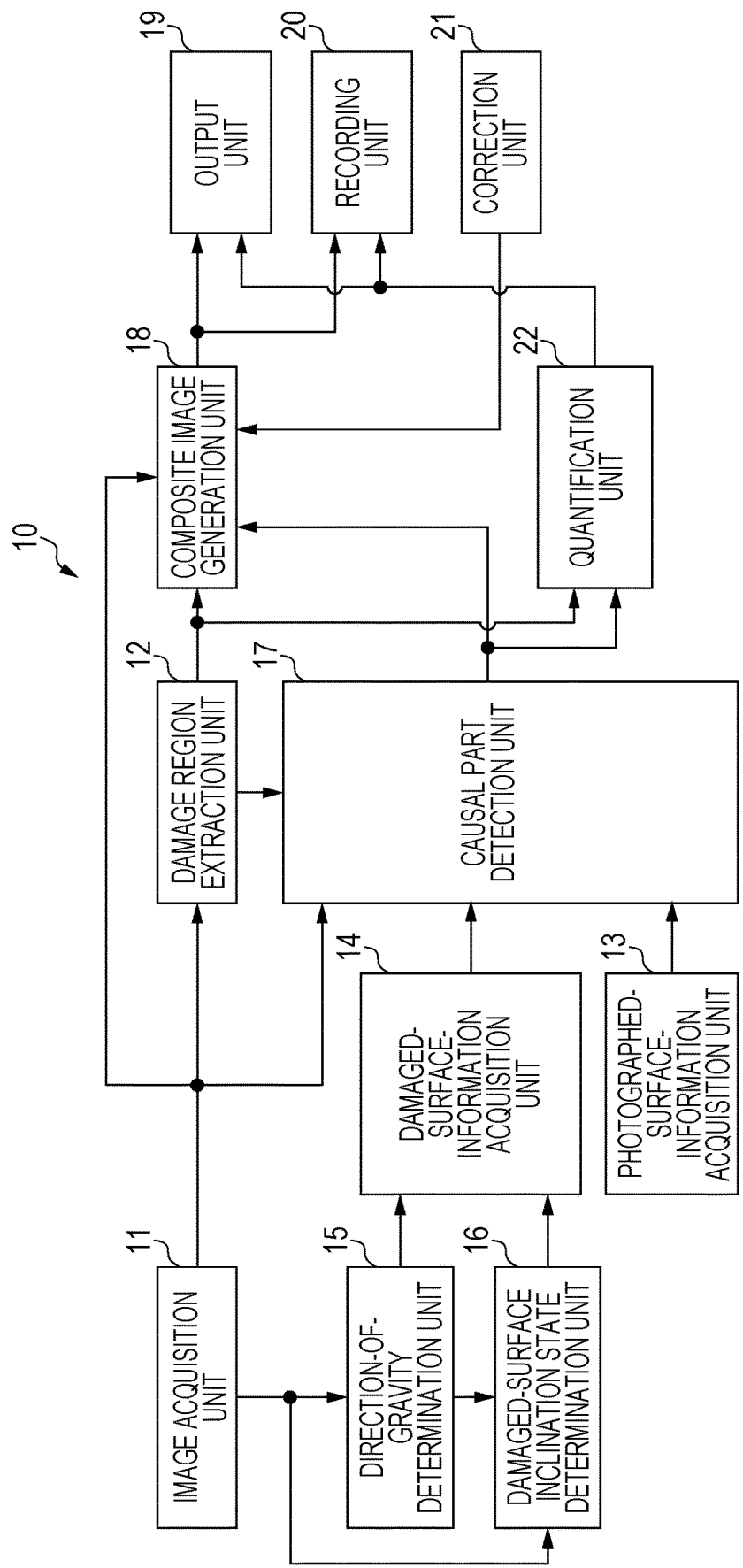
FIG. 12 is a functional block diagram illustrating a third embodiment of the inspection support apparatus.

FIG. 12 is a functional block diagram illustrating a third embodiment of the inspection support apparatus.

The inspection support apparatus 10 of this embodiment is different from the inspection support apparatus 10 of the first and second embodiments described above in that the inspection support apparatus 10 of this embodiment further includes a quantification unit 22 that quantifies a damage region and a causal part. Only the part different from the inspection support apparatus 10 of the above-described first and second embodiments is described below.

The quantification unit 22 obtains the area and/or color of an extracted damage region on the basis of the result of extraction by the damage region extraction unit 12 to quantify the damage region. Further, the quantification unit 22 obtains at least one of, for example, the width, length, or area of a detected causal part on the basis of the result of detection by the causal part detection unit 17 to quantify the causal part. Specifically, for a crack, a construction joint, and a joint, the quantification unit 22 obtains the width, length, etc. from the image to quantify the crack, construction joint, and joint. For peeling, the quantification unit 22 obtains the area, etc. from the image to quantify the peeling. As the method for quantification, publicly known methods for image measurement can be employed.

FIG. 13 is a diagram illustrating example quantification.

In the example illustrated in FIG. 13, each extracted damage region is assigned an ID (identification) and numbered, and the type and area of the damage region are obtained to quantify the damage region. Further, for each damage region, the type, width, length, and area of the causal part are obtained to quantify the causal part.

The output unit 19 outputs information obtained by quantifying the result of extraction of the damage region and the result of detection of the causal part to a display together with the composite image or separately from the composite image. The recording unit 20 records the quantified information.

As described above, in addition to extraction of a damage region and detection of a causal part relating to the damage region, quantification of the results of extraction and detection is also performed automatically. Accordingly, the load of inspection can be significantly reduced.

Note that a configuration in which both the damage region and the causal part are quantified is employed in this embodiment; however, a configuration in which only one of the results is quantified can be employed.

Fourth Embodiment

Figure 14:
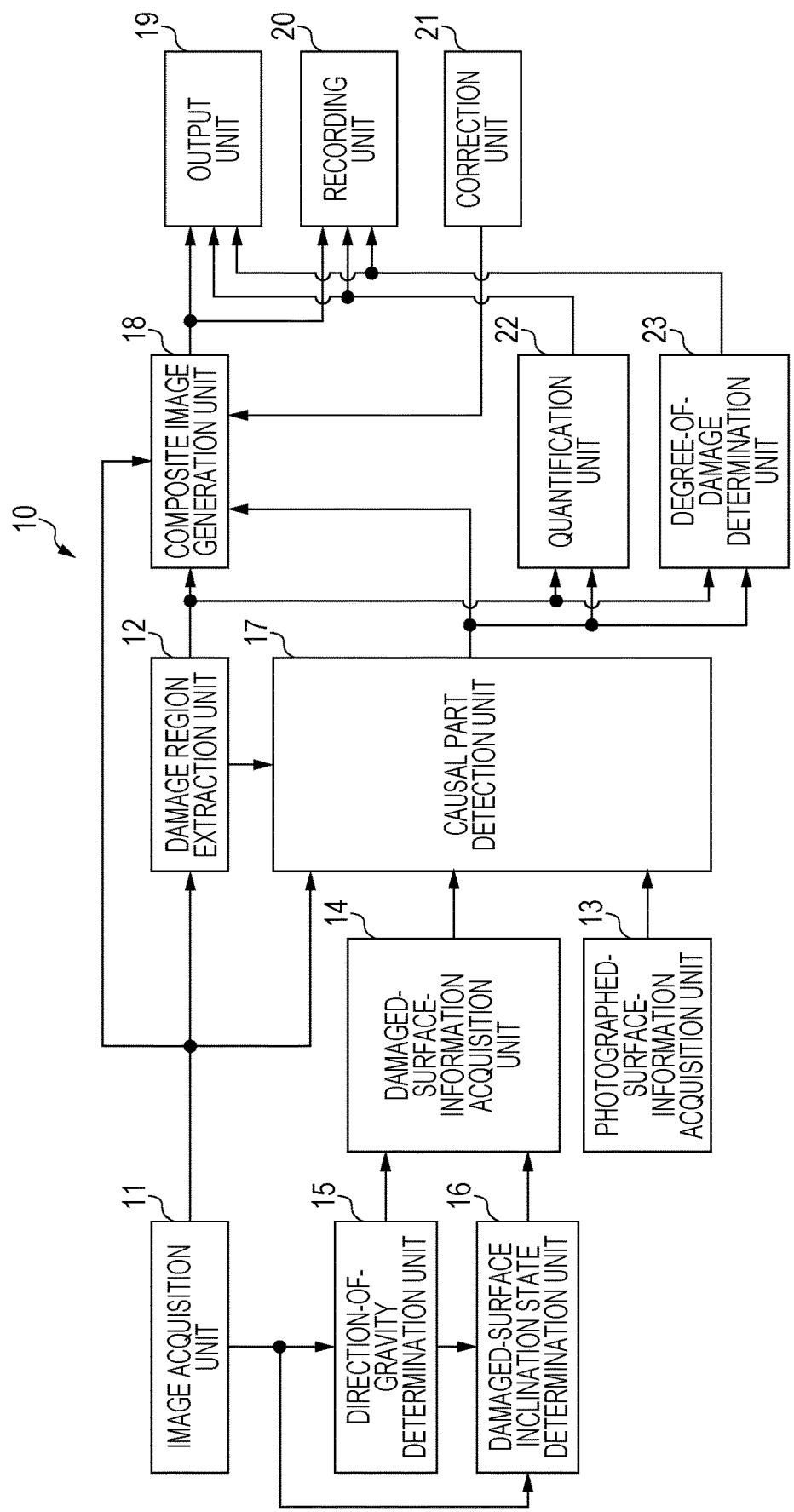
FIG. 14 is a functional block diagram illustrating a fourth embodiment of the inspection support apparatus.

FIG. 14 is a functional block diagram illustrating a fourth embodiment of the inspection support apparatus.

The inspection support apparatus 10 of this embodiment is different from the inspection support apparatus 10 of the first to third embodiments described above in that the inspection support apparatus 10 of this embodiment further includes a degree-of-damage determination unit 23 that determines the degree of damage on the basis of the result of extraction of a damage region and the result of detection of a causal part. Only the part different from the inspection support apparatus 10 of the above-described first to third embodiments is described below.

The degree-of-damage determination unit 23 acquires the result of extraction of a damage region and the result of detection of a causal part and determines the degree of damage in accordance with predetermined criteria. As the criteria, independently established criteria or criteria established by the country, the local government, the enterprise, etc. can be used. For example, criteria defined in the bridge regular inspection manual established by the Ministry of Land, Infrastructure and Transport regarding inspection of bridges can be used.

In the determination, for example, an evaluation category among the predetermined evaluation categories to which the damage belongs is determined. For example, the degree of damage is divided into five categories including category a, category b, category c, category d, and category e in ascending order of degree of damage, and conditions based on which damage is determined to belong to each category are defined. The degree-of-damage determination unit 23 determines a category to which the damage belongs on the basis of the result of extraction of the damage region and the result of detection of the causal part.

The output unit 19 outputs the result of determination of the degree of damage to a display together with the composite image or separately from the composite image. The recording unit 20 records the result of determination of the degree of damage.

As described above, the degree of damage is automatically determined and output. Accordingly, the load of inspection can be significantly reduced.

Fifth Embodiment

Figure 15:
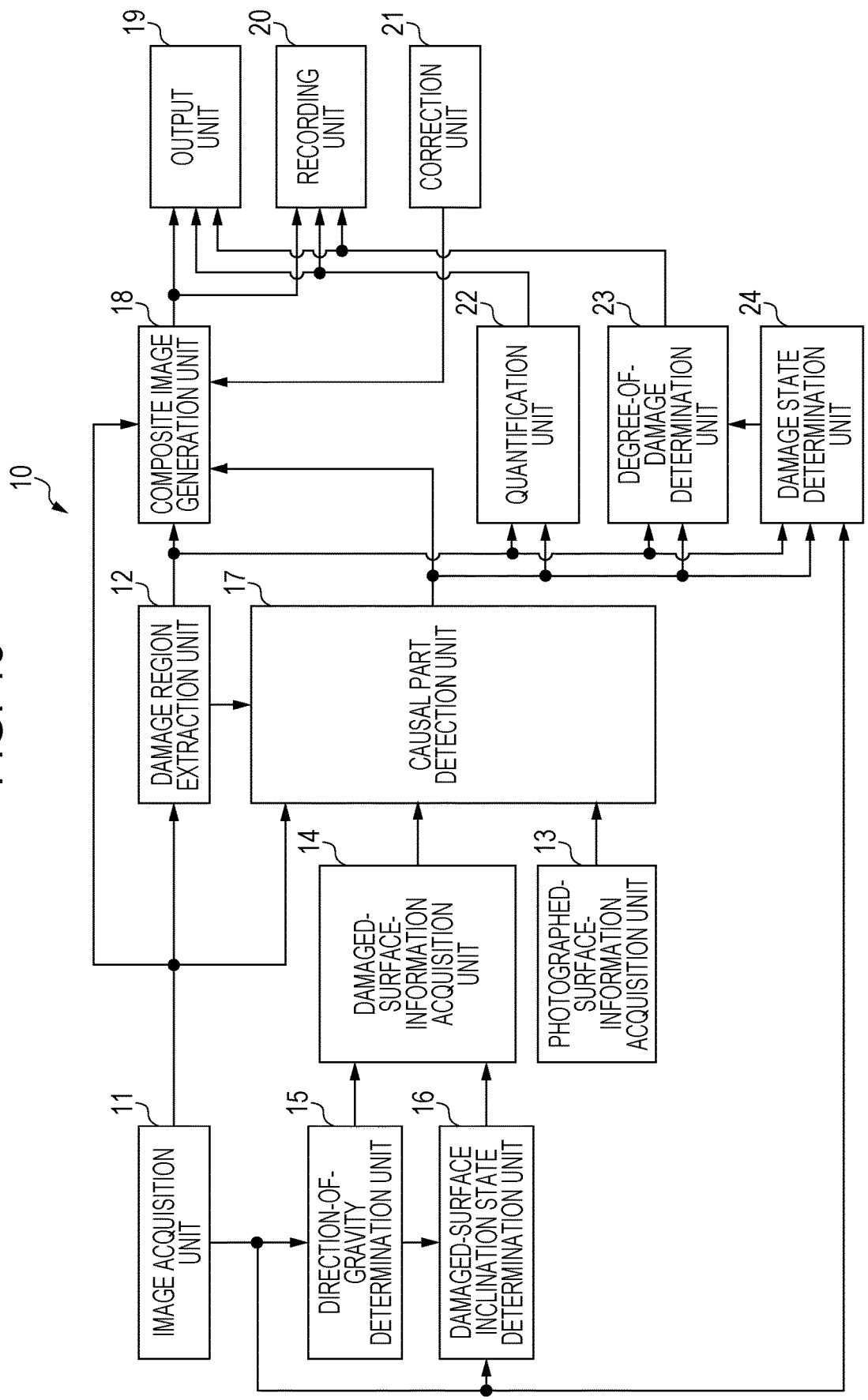
FIG. 15 is a functional block diagram illustrating a fifth embodiment of the inspection support apparatus.

FIG. 15 is a functional block diagram illustrating a fifth embodiment of the inspection support apparatus.

The inspection support apparatus 10 of this embodiment is different from the inspection support apparatus 10 according to the fourth embodiment described above in that the inspection support apparatus 10 of this embodiment further includes a damage state determination unit 24 that determines, in a case where a damage region is extracted, the damage state from the image. Only the part different from the inspection support apparatus 10 of the above-described fourth embodiment is described below.

The damage state determination unit 24 determines the damage state by image recognition. The damage state here means "features of damage". For example, in a case where a water leakage region is extracted as a damage region, it is determined, for example, whether mud is mixed or dripping rust is mixed into the water leakage. In a case where a free lime region is extracted as a damage region, it is determined, for example, whether or not free lime in the shape of icicles is present.

For the image recognition, various methods can be employed. For example, a configuration can be employed in which a trained model subjected to machine learning using images that include damage as learning data is used to determine the damage state.

The degree-of-damage determination unit 23 determines the degree of damage on the basis of the result of extraction of the damage region, the result of detection of the causal part, and the result of determination of the damage state.

FIG. 16 is a diagram illustrating example evaluation categories of the degree of damage.

In the example illustrated in FIG. 16, the degree of damage is divided into five categories including category a, category b, category c, category d, and category e in ascending order of degree of damage.

The degree-of-damage determination unit 23 determines an evaluation category to which the damage belongs on the basis of the result of extraction of the damage region, the result of detection of the causal part, and the result of determination of the damage state.

As described above, the degree of damage can be determined more appropriately by taking into consideration the damage state. Further, determination conforming to predetermined criteria (for example, criteria established by the country, the local government, etc.) can be performed.

Note that in a case where a plurality of damage regions are extracted from an image, the degree-of-damage determination unit 23 selects a type of damage that is used in determination such that the degree of damage is evaluated as severe damage. For example, it is assumed that the degree of severity of damage is defined in the order of "water leakage"< "free lime"< "water leakage including dripping rust" (the degree of severity of damage of "free lime" is higher than that of "water leakage" and the degree of severity of damage of "water leakage including dripping rust" is higher than that of "free lime"). In this case, in a case where, for example, water leakage and free lime are simultaneously occurring, free lime is selected as the type of damage that is used in determination. In a case where, for example, water leakage including dripping rust and free lime are simultaneously occurring, water leakage including dripping rust is selected as the type of damage that is used in determination. Accordingly, the degree of damage can be determined more appropriately.

Modifications

Processing Target Image

As described above, an image that is processed in the inspection support apparatus may be an image obtained by photographing the entire surface that is an inspection target or may be an image obtained by photographing only a part of the surface.

The inspection support apparatus 10 may further include a function (panorama composition function) of, in a case where a group of images is obtained by dividing the entire surface into a plurality of regions and photographing the regions, combining the group of images to generate one image.

Further, as a processing target image, a moving image can be acquired. A moving image can be regarded as a group of time-series still images. In this case, processing is performed on a per frame basis. Alternatively, one still image (a still image of an inspection target surface) is generated from a moving image of the inspection target surface, and the process for extracting a damage region, etc. may be performed for the generated still image.

In a case where a group of images is acquired by dividing the entire surface into a plurality of regions and photographing the regions and where the process for extracting a damage region, etc. is performed for each image, to output the results, one composite image may be generated and output.

Modification of Damage Region Extraction Unit

In the above-described embodiments, in addition to extracting a damage region, the damage region extraction unit 12 is configured to also determine the type of damage; however, the damage region extraction unit 12 at least needs to be capable of extracting a damage region.

Modification of Causal Part Detection Unit

In the above-described embodiments, in addition to detecting a causal part, the causal part detection unit 17 is configured to also determine the type of the detected causal part; however, the causal part detection unit 17 at least needs to be capable of detecting a causal part. Regarding a causal part, the causal part detection unit 17 needs to be configured so as to be capable of detecting at least one of a crack, a construction joint, a joint, or peeling.

Modification of Output of Results

In the above-described embodiments, a configuration is employed in which as the result of extraction of a damage region and the result of detection of a causal part, a composite image is generated and the generated composite image is output to a display; however, the form of output of the results is not limited to this. For example, in a case where the results are quantified, the quantified information (for example, the dimensions of damage and those of the cause of damage, etc.) may be output in a predetermined file format (for example, a CSV (comma separated value) file, etc.). Alternatively, the result of extraction of a damage region and the result of detection of a causal part may be output as a CAD (computer-aided design) file. That is, a CAD drawing of a concrete structure that is an inspection target is used, and the extracted damage region and the causal part are added to the CAD drawing and output. When the results are output as a CAD file as described above, the CAD file can be used as a damage diagram as is.

In a case where the type of damage is determined, the result of determination of the type of damage may be output. For example, a configuration may be employed in which the type of damage is displayed on a display together with the composite image. Similarly, in a case where the type of cause is determined, the result of determination of the type of cause may also be output.

Further, in a case where the type of damage is output, when a plurality of damage regions are extracted, a configuration may be employed in which damage of a higher degree of severity is preferentially output (displayed). For example, it is assumed that the degree of severity of damage is defined in the order of "water leakage"< "free lime"< "water leakage including dripping rust". In this case, in a case where, for example, water leakage and free lime are simultaneously occurring, free lime is determined to be the type of damage and is output (displayed). In a case where, for example, water leakage including dripping rust and free lime are simultaneously occurring, water leakage including dripping rust is determined to be the type of damage and is output (displayed).

Modification of Hardware Configuration

Hardware for implementing the inspection support apparatus of the present invention can be formed of various processors. The various processors include a CPU (central processing unit), which is a general-purpose processor executing a program to function as various processing units, a programmable logic device (PLD), such as an FPGA (field-programmable gate array), which is a processor having a circuit configuration that is changeable after manufacture, and a dedicated electric circuit, such as an ASIC (application-specific integrated circuit), which is a processor having a circuit configuration specifically designed to perform specific processing. One processing unit that constitutes the inspection support apparatus may be configured as one of the various processors described above or two or more processors of the same type or different types. For example, one processing unit may be configured as a plurality of FPGAs or a combination of a CPU and an FPGA. Further, a plurality of processing units may be configured as one processor. As the first example of configuring a plurality of processing units as one processor, a form is possible where one processor is formed of a combination of one or more CPUs and software, and the processor functions as the plurality of processing units, a representative example of which is a computer, such as a client or a server. As the second example thereof, a form is possible where a processor is used in which the functions of the entire system including the plurality of processing units are implemented as one IC (integrated circuit) chip, a representative example of which is a system on chip (SoC). As described above, regarding the hardware configuration, the various processing units are configured by using one or more of the various processors described above. Further, the hardware configuration of the various processors is more specifically an electric circuit (circuitry) in which circuit elements, such as semiconductor elements, are combined.

Further, a configuration can be employed in which a computer on a network performs a process including extraction of a damage region, detection of a causal part, etc. and transmits the results to a user's terminal (that is, cloud computing).

Figure 17:
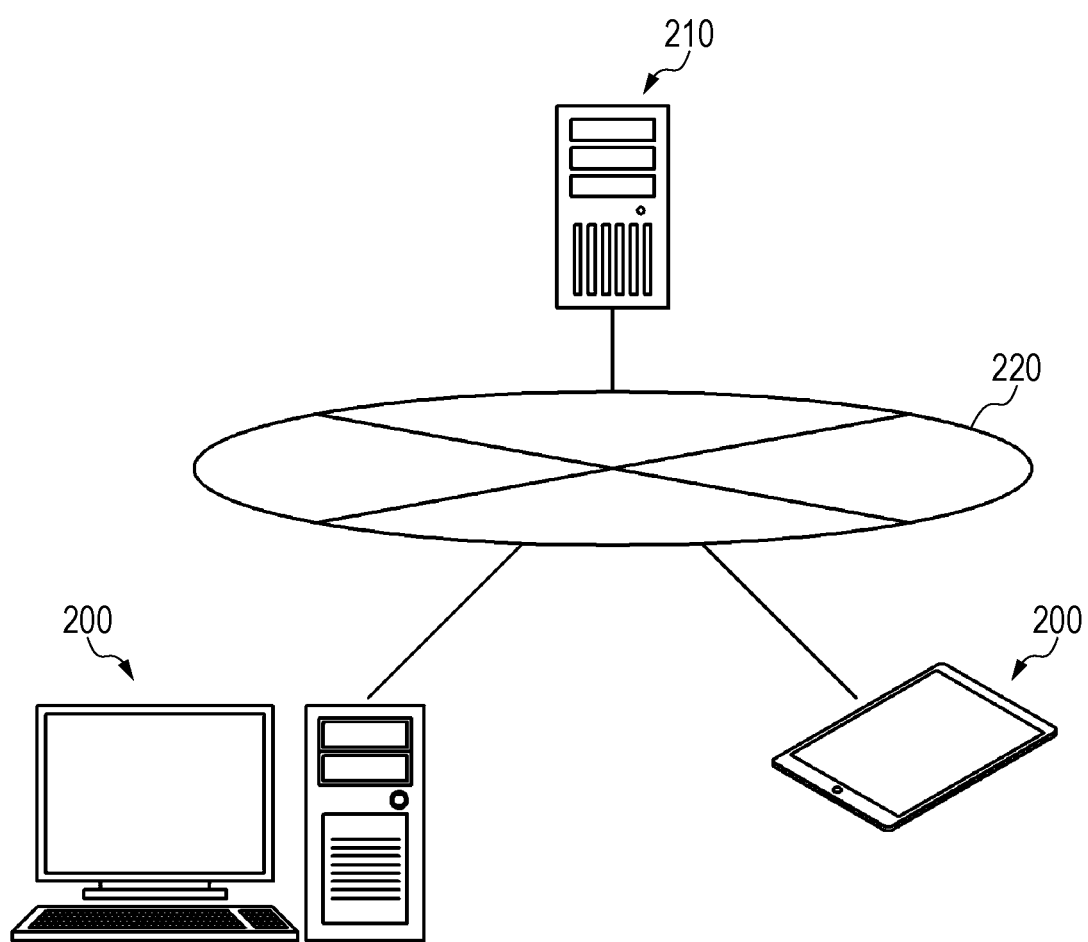
FIG. 17 is a diagram illustrating an example system configuration in a case where a process including extraction of a damage region, detection of a causal part, etc. is performed by a computer on a network.

FIG. 17 is a diagram illustrating an example system configuration in a case where a process including extraction of a damage region, detection of a causal part, etc. is performed by a computer on a network.

A user's terminal 200 and a server 210 are connected to each other via a communication network 220 such that communication is possible. The communication network 220 is formed of, for example, a LAN (local area network) or the Internet. The user's terminal 200 is formed of a personal computer, a tablet terminal, a PDA (personal data assistance), a smartphone, etc. The server 210 executes the inspection support program to function as the inspection support apparatus.

The user transmits an image of an inspection target to the server 210 from the terminal 200. The server 210 receives (acquires) the image transmitted from the user's terminal 200 and performs a process for extracting a damage region, a process for detecting a causal part, etc. The server 210 transmits (outputs) the results to the user's terminal 200. The user's terminal 200 receives and displays on a display unit (display) the result of extraction of a damage region and the result of detection of a causal part transmitted from the server 210.

Note that the terminal 200 that transmits an image of an inspection target and the terminal 200 that receives the result of extraction of a damage region and the result of detection of a causal part may be different terminals.

In the embodiments described above, A non-transitory computer readable recording medium storing an inspection support apparatus, an inspection support method, and an inspection support program for a concrete structure stated in (1) to (21) below are described.

(1) An inspection support apparatus for a concrete structure, the inspection support apparatus including: an image acquisition unit that acquires an image obtained by photographing a concrete structure that is an inspection target; a damage region extraction unit that extracts from the image, a damage region appearing on a surface of the concrete structure; a causal part detection unit that detects, in a case where the damage region is extracted, a causal part causing damage from the image on the basis of a result of extraction of the damage region; and an output unit that outputs the result of extraction of the damage region and a result of detection of the causal part.

According to this form, the damage region appearing on the surface of the concrete structure is automatically extracted from the image obtained by photographing the concrete structure that is an inspection target. In the case where the damage region is extracted, the causal part causing damage is automatically detected from the image on the basis of the result of extraction of the damage region. Accordingly, the damage region and the causal part relating to the damage region can be automatically detected, and the load of inspection can be reduced.

(2) The inspection support apparatus for a concrete structure according to (1) described above, in which the causal part detection unit detects the causal part from within the damage region.

According to this form, in the case where the damage region is extracted, the causal part is detected from within the damage region. It is often the case that the causal part causing damage is present within the damage region. Therefore, the causal part can be detected efficiently by searching from damage region.

(3) The inspection support apparatus for a concrete structure according to (1) or (2) described above, further including a photographed-surface-information acquisition unit that acquires information about a photographed surface of the concrete structure, in which the causal part detection unit detects the causal part from the image on the basis of the result of extraction of the damage region and the information about the photographed surface.

According to this form, information about the photographed surface of the concrete structure is acquired, and the information about the photographed surface is used to detect the causal part. Accordingly, the causal part can be detected more efficiently.

(4) The inspection support apparatus for a concrete structure according to any one of (1) to (3) described above, further including a damaged-surface-information acquisition unit that acquires information about a damaged surface from which the damage region is extracted, in which the causal part detection unit detects the causal part from the image on the basis of the result of extraction of the damage region and the information about the damaged surface.

According to this form, information about the damaged surface from which the damage region is extracted is acquired, and the information about the damaged surface is used to detect the causal part. Accordingly, the causal part can be detected more efficiently.

(5) The inspection support apparatus for a concrete structure according to (4) described above, in which the damaged-surface-information acquisition unit acquires as the information about the damaged surface, information about a direction of gravity and about an inclination state of the damaged surface relative to the direction of gravity.

According to this form, information about the direction of gravity and about the inclination state of the damaged surface relative to the direction of gravity is acquired as the information about the damaged surface. The damage region is affected by gravity and changes in the way of spreading. Therefore, the causal part can be detected efficiently by acquiring the information to detect the causal part.

(6) The inspection support apparatus for a concrete structure according to (5) described above, further including a direction-of-gravity determination unit that determines the direction of gravity from the image, in which the damaged-surface-information acquisition unit acquires the information about the direction of gravity from the direction-of-gravity determination unit.

According to this form, the direction of gravity is determined from the acquired image. For example, the direction of gravity is determined by image recognition, etc.

(7) The inspection support apparatus for a concrete structure according to (6) described above, in which the direction-of-gravity determination unit determines the direction of gravity on the basis of a shape of a spread of the damage region and/or a state of damage.

According to this form, the direction of gravity is determined on the basis of the shape of the spread of the damage region and/or the state of damage. The damage region is affected by gravity and changes in the shape of the spread. Therefore, the direction of gravity can be determined from the shape of the spread of the damage region. Further, the state of damage, such as free lime in the shape of icicles, etc., is also affected by gravity. Therefore, the direction of gravity can also be determined from the state of damage.

(8) The inspection support apparatus for a concrete structure according to any one of (5) to (7) described above, further including a damaged-surface inclination state determination unit that determines, from the image, the inclination state of the damaged surface relative to the direction of gravity, in which the damaged-surface-information acquisition unit acquires the information about the inclination state of the damaged surface relative to the direction of gravity from the damaged-surface inclination state determination unit.

According to this form, the inclination state of the damaged surface relative to the direction of gravity is determined from the acquired image. For example, the shape of the spread of the damage region is determined from the image, and the inclination state of the damaged surface is determined from the shape.

(9) The inspection support apparatus for a concrete structure according to any one of (5) to (7) described above, in which the causal part detection unit detects the causal part while a central part of the damage region is weighted in a case where an inclination of the damaged surface is greater than or equal to a threshold value, and detects the causal part while a part on an upper side of the damage region in direction of gravity is weighted in a case where the inclination of the damaged surface is less than the threshold value.

According to this form, in the case where the inclination of the damaged surface is greater than or equal to the threshold value, a central part of the damage region is weighted to detect the causal part. On the other hand, in the case where the inclination of the damaged surface is less than the threshold value, a part on the upper side of the damage region in the direction of gravity is weighted to detect the causal part. That is, in the case where the damaged surface is at a right angle or at close to a right angle to the direction of gravity, a central part of the damage region is weighted to detect the causal part. This is because in such a case, the probability of the causal part being present in a central part of the damage region is high. On the other hand, in the case where the damaged surface is not at a right angle to the direction of gravity (excluding the case where the damaged surface is at close to a right angle to the direction of gravity), a part on the upper side of the damage region in the direction of gravity is weighted to detect the causal part. This is because in such a case, the probability of the causal part being present in a part on the upper side of the damage region in the direction of gravity is high.

(10) The inspection support apparatus for a concrete structure according to any one of (1) to (9) described above, in which the damage region extraction unit extracts the damage region on the basis of a brightness distribution and/or an RGB-value distribution of the image.

According to this form, the damage region is extracted on the basis of the brightness distribution and/or the RGB-value distribution of the image. The damage region has a brightness distribution and an RGB-value distribution different from those of the other region. Therefore, the damage region can be extracted on the basis of the brightness distribution and/or the RGB-value distribution of the image.

(11) The inspection support apparatus for a concrete structure according to any one of (1) to (10) described above, in which the damage region extraction unit extracts as the damage region, a free lime region and/or a water leakage region appearing on the surface of the concrete structure.

According to this form, the free lime region and/or the water leakage region appearing on the surface of the concrete structure can be extracted as the damage region.

(12) The inspection support apparatus for a concrete structure according to any one of (1) to (11) described above, in which the causal part detection unit detects as the causal part, at least one of a crack part, a construction joint part, a joint part, or a peeling part.

According to this form, at least one of a crack part, a construction joint part, a joint part, or a peeling part is detected as the causal part. Damage, such as water leakage, free lime, etc., is caused by a crack, a construction joint, a joint, or peeling. Therefore, when such a part is detected, the causal part can be detected appropriately.

(13) The inspection support apparatus for a concrete structure according to any one of (1) to (12) described above, further including a composite image generation unit that generates a composite image obtained by adding a frame that surrounds the damage region and a line that traces the causal part to the image, in which the output unit outputs the composite image to a display device as the result of extraction of the damage region and the result of detection of the causal part.

According to this form, the composite image obtained by adding the frame surrounding the damage region and the line tracing the causal part to the image is generated and output to the display device. Accordingly, the damage region and the causal part can be grasped at a glance.

(14) The inspection support apparatus for a concrete structure according to (13) described above, further including a correction unit that corrects the result of extraction of the damage region and the result of detection of the causal part.

According to this form, the function of correcting the result of extraction of the damage region and the result of detection of the causal part is included. Accordingly, erroneous extraction and erroneous detection can be corrected as appropriate.

(15) The inspection support apparatus for a concrete structure according to any one of (1) to (14) described above, further including a quantification unit that quantifies the damage region and/or the causal part, in which the output unit further outputs information about the quantified damage region and/or the quantified causal part.

According to this form, the damage region and/or the causal part are quantified and output. Accordingly, the degree of damage can be grasped more easily.

(16) The inspection support apparatus for a concrete structure according to (15) described above, in which the quantification unit quantifies the damage region by obtaining an area and/or a color of the damage region, and quantifies the causal part by obtaining at least one of a width, a length, or an area of the causal part.

According to this form, the area and/or the color of the damage region are obtained to quantify the damage region. Further, at least one of the width, the length, or the area of the causal part is obtained to quantify the causal part.

(17) The inspection support apparatus for a concrete structure according to any one of (1) to (16) described above, further including a degree-of-damage determination unit that determines a degree of damage on the basis of the result of extraction of the damage region and the result of detection of the causal part.

According to this form, the degree of damage is automatically determined on the basis of the result of extraction of the damage region and the result of detection of the causal part. Accordingly, the load of inspection can be further reduced.

(18) The inspection support apparatus for a concrete structure according to any one of (1) to (16) described above, further including a damage state determination unit that determines a damage state from the image in a case where the damage region is extracted.

According to this form, in the case where the damage region is extracted, the damage state is determined from the image. For example, for water leakage, the presence or absence of dripping rust, the presence or absence of mixed mud, etc. is determined, and for free lime, the shape of the free lime (the shape of icicles, etc.) is determined.

(19) The inspection support apparatus for a concrete structure according to (18) described above, further including a degree-of-damage determination unit that determines a degree of damage on the basis of the result of extraction of the damage region, the result of detection of the causal part, and a result of determination of the damage state.

According to this form, the degree of damage is determined on the basis of the result of extraction of the damage region, the result of detection of the causal part, and the result of determination of the damage state. Accordingly, the degree of damage can be determined more appropriately.

(20) An inspection support method for a concrete structure, the inspection support method including: a step of acquiring an image obtained by photographing a concrete structure that is an inspection target; a step of extracting, from the image, a damage region appearing on a surface of the concrete structure; a step of detecting, in a case where the damage region is extracted, a causal part causing damage from the image on the basis of a result of extraction of the damage region; and a step of outputting the result of extraction of the damage region and a result of detection of the causal part.

According to this form, the damage region appearing on the surface of the concrete structure is extracted from the image obtained by photographing the concrete structure that is an inspection target. In the case where the damage region is extracted, the causal part causing damage is detected from the image on the basis of the result of extraction of the damage region. Accordingly, the damage region and the causal part relating to the damage region can be automatically detected, and the load of inspection can be reduced.

(21) A non-transitory computer readable recording medium storing an inspection support program for a concrete structure, the inspection support program causing a computer to implement: a function of acquiring an image obtained by photographing a concrete structure that is an inspection target; a function of extracting, from the image, a damage region appearing on a surface of the concrete structure; a function of detecting, in a case where the damage region is extracted, a causal part causing damage from the image on the basis of a result of extraction of the damage region; and a function of outputting the result of extraction of the damage region and a result of detection of the causal part.

According to this form, the damage region appearing on the surface of the concrete structure is extracted from the image obtained by photographing the concrete structure that is an inspection target. In the case where the damage region is extracted, the causal part causing damage is detected from the image on the basis of the result of extraction of the damage region. Accordingly, the damage region and the causal part relating to the damage region can be automatically detected, and the load of inspection can be reduced.

Based on the above description, an inspection support apparatus according to Additional Statement 1 below can be grasped.

Additional Statement 1

An inspection support apparatus for a concrete structure, the inspection support apparatus including a processor, the processor acquiring an image obtained by photographing a concrete structure that is an inspection target, extracting, from the image, a damage region appearing on a surface of the concrete structure, detecting, in a case where the damage region is extracted, a causal part causing damage from the image on the basis of a result of extraction of the damage region, and outputting the result of extraction of the damage region and a result of detection of the causal part.

REFERENCE SIGNS LIST 10 inspection support apparatus
11 image acquisition unit
12 damage region extraction unit
13 photographed-surface-information acquisition unit
14 damaged-surface-information acquisition unit
15 direction-of-gravity determination unit
16 damaged-surface inclination state determination unit
17 causal part detection unit
18 composite image generation unit
19 output unit
20 recording unit
21 correction unit
22 quantification unit
23 degree-of-damage determination unit
24 damage state determination unit
100 computer
101 CPU
104 HDD
105 communication IF
106 input-output IF
107 optical disk drive
200 terminal
210 server
220 communication network
F frame surrounding damage region
L line tracing causal part
V gravity vector
S1 to S6 procedure of inspection support process by inspection support apparatus

What is claimed is:

1. An inspection support apparatus for a concrete structure, the inspection support apparatus comprising a processor configured to:

acquire an image obtained by photographing a concrete structure that is an inspection target;

extract, from the image, a damage region appearing on a surface of the concrete structure;

detect, in a case where the damage region is extracted, a causal part causing damage from the image on the basis of a result of extraction of the damage region;

output the result of extraction of the damage region and a result of detection of the causal part;

acquire information about a damaged surface from which the damage region is extracted;

detect the causal part from the image on the basis of the result of extraction of the damage region and the information about the damaged surface;

acquire as the information about the damaged surface, information about a direction of gravity and about an inclination state of the damaged surface relative to the direction of gravity;

detect the causal part while a central part of the damage region is weighted in a case where an inclination of the damaged surface is greater than or equal to a threshold value; and detect the causal part while a part on an upper side of the damage region in direction of gravity is weighted in a case where the inclination of the damaged surface is less than the threshold value.

2. The inspection support apparatus for a concrete structure according to claim 1, wherein the processor is further configured to detect the causal part from within the damage region.

3. The inspection support apparatus for a concrete structure according to claim 1, wherein the processor is further configured to acquire information about a photographed surface of the concrete structure, and detect the causal part from the image on the basis of the result of extraction of the damage region and the information about the photographed surface.

4. The inspection support apparatus for a concrete structure according to claim 1, wherein the processor is further configured to determine the direction of gravity from the image, and acquire the information about the direction of gravity.

5. The inspection support apparatus for a concrete structure according to claim 4, wherein the processor is further configured to determine the direction of gravity on the basis of a shape of a spread of the damage region and/or a state of damage.

6. The inspection support apparatus for a concrete structure according to claim 1, wherein the processor is further configured to determine, from the image, the inclination state of the damaged surface relative to the direction of gravity.

7. The inspection support apparatus for a concrete structure according to claim 1, wherein the processor is further configured to extract as the damage region, a free lime region and/or a water leakage region appearing on the surface of the concrete structure.

8. The inspection support apparatus for a concrete structure according to claim 1, wherein the processor is further configured to detect as the causal part, at least one of a crack part, a construction joint part, a joint part, or a peeling part.

9. The inspection support apparatus for a concrete structure according to claim 1, wherein the processor is further configured to generate a composite image obtained by adding a frame that surrounds the damage region and a line that traces the causal part to the image, and output the composite image to a display device as the result of extraction of the damage region and the result of detection of the causal part.

10. The inspection support apparatus for a concrete structure according to claim 9, wherein the processor is further configured to correct the result of extraction of the damage region and the result of detection of the causal part.

11. The inspection support apparatus for a concrete structure according to claim 1, wherein the processor is further configured to quantify the damage region and/or the causal part, and output information about the quantified damage region and/or the quantified causal part.

12. The inspection support apparatus for a concrete structure according to claim 11, wherein the processor is further configured to quantify the damage region by obtaining an area and/or a color of the damage region, and quantify the causal part by obtaining at least one of a width, a length, or an area of the causal part.

13. The inspection support apparatus for a concrete structure according to claim 1, wherein the processor is further configured to determine a degree of damage on the basis of the result of extraction of the damage region and the result of detection of the causal part.

14. The inspection support apparatus for a concrete structure according to claim 1, wherein the processor is further configured to determine a damage state from the image in a case where the damage region is extracted.

15. The inspection support apparatus for a concrete structure according to claim 14, wherein the processor is further configured to determine a degree of damage on the basis of the result of extraction of the damage region, the result of detection of the causal part, and a result of determination of the damage state.

16. An inspection support method for a concrete structure, the inspection support method comprising:

acquiring an image obtained by photographing a concrete structure that is an inspection target;

extracting, from the image, a damage region appearing on a surface of the concrete structure;

detecting, in a case where the damage region is extracted, a causal part causing damage from the image on the basis of a result of extraction of the damage region;

outputting the result of extraction of the damage region and a result of detection of the causal part;

acquiring information about a damaged surface from which the damage region is extracted;

detecting the causal part from the image on the basis of the result of extraction of the damage region and the information about the damaged surface;

acquiring as the information about the damaged surface, information about a direction of gravity and about an inclination state of the damaged surface relative to the direction of gravity;

detecting the causal part while a central part of the damage region is weighted in a case where an inclination of the damaged surface is greater than or equal to a threshold value; and detecting the causal part while a part on an upper side of the damage region in direction of gravity is weighted in a case where the inclination of the damaged surface is less than the threshold value.

17. A non-transitory computer readable recording medium storing an inspection support program for a concrete structure, the inspection support program causing a computer to implement:

a function of acquiring an image obtained by photographing a concrete structure that is an inspection target;

a function of extracting, from the image, a damage region appearing on a surface of the concrete structure;

a function of detecting, in a case where the damage region is extracted, a causal part causing damage from the image on the basis of a result of extraction of the damage region;

a function of outputting the result of extraction of the damage region and a result of detection of the causal part;

a function of acquiring information about a damaged surface from which the damage region is extracted;

a function of detecting the causal part from the image on the basis of the result of extraction of the damage region and the information about the damaged surface;

a function of acquiring as the information about the damaged surface, information about a direction of gravity and about an inclination state of the damaged surface relative to the direction of gravity;

a function of detecting the causal part while a central part of the damage region is weighted in a case where an inclination of the damaged surface is greater than or equal to a threshold value; and a function of detecting the causal part while a part on an upper side of the damage region in direction of gravity is weighted in a case where the inclination of the damaged surface is less than the threshold value.

* * * * *